US012784187B2

(12) United States Patent
Abe et al.

(10) Patent No.: US 12,784,187 B2
(45) Date of Patent: Nov. 3, 2026

(54) DIAGNOSTIC SUPPORT PROGRAM

(71) Applicants: Paramevia PTE. Ltd., The Central (SG); Mediott Co., Ltd., Tokyo (JP)

(72) Inventors: Takehiko Abe, The Central (SG); Norifumi Yoshida, The Central (SG)

(73) Assignees: RADWISP PTE. LTD., Singapore (SG); MEDIOTT CO., LTD., Tokyo (JP)

( * ) Notice: Subject to any disclaimer, the term of this patent is extended or adjusted under 35 U.S.C. 154(b) by 768 days.

(21) Appl. No.: 17/621,218

(22) PCT Filed: Jul. 6, 2020

(86) PCT No.: PCT/JP2020/026482

§ 371 (c)(1),
(2) Date: Dec. 20, 2021

(87) PCT Pub. No.: WO2021/002478

PCT Pub. Date: Jan. 7, 2021

(65) Prior Publication Data

US 2022/0398720 A1 Dec. 15, 2022

(30) Foreign Application Priority Data

Jul. 4, 2019 (JP) ................................ 2019-125444
Aug. 22, 2019 (JP) ................................ 2019-152401

(51) Int. Cl.
*G06T 7/00* (2017.01)
*A61B 5/00* (2006.01)
(Continued)

(52) U.S. Cl.
CPC ............ *G06T 7/0012* (2013.01); *A61B 5/055* (2013.01); *A61B 6/463* (2013.01); *A61B 6/503* (2013.01);
(Continued)

(58) Field of Classification Search
CPC . G06T 7/0012; G06T 7/11; G06T 7/13; G06T 7/90; G06T 7/20;
(Continued)

(56) References Cited

U.S. PATENT DOCUMENTS 10,026,016 B2 7/2018 Tewfik et al.
11,004,201 B2 * 5/2021 Abe ...................... G16H 10/60
(Continued)

FOREIGN PATENT DOCUMENTS

CN 106175766 A 12/2016
EP 3488782 A1 * 5/2019 ............ A61B 5/024
(Continued)

OTHER PUBLICATIONS

Bianconi, Francesco, et al. "Theoretical and experimental comparison of different approaches for color texture classification." Journal of Electronic Imaging 20.4 (2011): 043006-043006.*
(Continued)

*Primary Examiner* — Shefali D Goradia
(74) *Attorney, Agent, or Firm* — Dennemeyer & Associates LLC

(57) ABSTRACT

A diagnostic support program that is possible to display a movement of an organ is provided.
A diagnostic support program that analyzes images of an organ of a human and displays analysis results, the program causing a computer to execute a process comprising: processing of acquiring a plurality of frame images, processing of calculating a cyclic change that characterizes a state of an organ between each of the frame images, processing of Fourier-transforming the cyclic change that characterizes the state of the organ, processing of extracting a spectrum in a fixed band including a spectrum corresponding to a frequency of a movement of an organ out of a spectrum obtained after the Fourier-transforming, processing of per-
(Continued)

CHANGE IN INTENSITY OF FREQUENCY COMPONENTS CLOSE TO HEARTBEAT

FOURIER ANALYSIS RESULTS INDICATING ONLY FREQUENCY COMPONENTS CLOSE TO HEARTBEAT forming inverse Fourier transform on the spectrum extracted from the fixed band, and processing of outputting each of the images after performing the inverse Fourier transform, is provided.

19 Claims, 14 Drawing Sheets

(51) Int. Cl.

| | |
|---|---|
| ***A61B 5/055*** | (2006.01) |
| ***A61B 6/00*** | (2006.01) |
| ***A61B 6/46*** | (2024.01) |
| ***A61B 6/50*** | (2024.01) |
| ***G06T 7/11*** | (2017.01) |
| ***G06T 7/13*** | (2017.01) |
| ***G06T 7/20*** | (2017.01) |
| ***G06T 7/90*** | (2017.01) |

(52) U.S. Cl.
CPC .............. *A61B 6/5211* (2013.01); *G06T 7/11* (2017.01); *G06T 7/13* (2017.01); *G06T 7/20* (2013.01); *G06T 7/90* (2017.01); *G06T 2207/10088* (2013.01); *G06T 2207/10116* (2013.01); *G06T 2207/20056* (2013.01); *G06T 2207/30048* (2013.01); *G06T 2207/30061* (2013.01)

(58) Field of Classification Search
CPC . G06T 2207/10088; G06T 2207/10116; G06T 2207/20056; G06T 2207/30048; G06T 2207/30061; A61B 6/463; A61B 6/503; A61B 6/5211
See application file for complete search history.

(56) References Cited

U.S. PATENT DOCUMENTS

| | | | | |
|---|---|---|---|---|
| 12,469,140 | B2 * | 11/2025 | Sakaguchi | G06T 7/0016 |
| 2004/0102695 | A1 | 5/2004 | Stergiopoulos | |
| 2010/0090696 | A1 * | 4/2010 | Deimling | A61B 5/7253 324/309 |
| 2017/0287114 | A1 * | 10/2017 | Futamura | A61B 6/541 |
| 2017/0323440 | A1 * | 11/2017 | Tsunomori | G06T 7/13 |
| 2021/0052228 | A1 * | 2/2021 | Abe | G16H 50/20 |
| 2025/0061576 | A1 * | 2/2025 | Abe | A61B 6/03 |

FOREIGN PATENT DOCUMENTS

| | | | | | |
|---|---|---|---|---|---|
| JP | 2005-185387 | A | | 7/2005 | |
| JP | 2008-125616 | A | | 6/2008 | |
| JP | 2010187723 | A | * | 9/2010 | A61B 6/00 |
| JP | 2017-196410 | A | | 11/2017 | |
| JP | 6483875 | B1 | | 3/2019 | |
| WO | 2019-135412 | A1 | | 7/2019 | |

OTHER PUBLICATIONS

EPSR issued in EP patent application No. 20834791.4 mailed on Jun. 26, 2023.
International Search Report issued in connection with PCT Application No. PCT/JP2020/026482 dated Sep. 15, 2020.
Ziosoft's Vision, advanced medical imaging. (Online) https://www.zio.co.jp/en/ 5 pages, copyright 2018 Ziosoft, Inc.

* cited by examiner

DIAGNOSTIC SUPPORT PROGRAM

CROSS-REFERENCE TO RELATED APPLICATIONS

This is a 35 U.S.C. 371 National Stage Patent Application of International Application No. PCT/JP2020/026482, filed Jul. 6, 2020, which claims priority to Japanese applications JP 2019-125444 filed Jul. 4, 2019 and JP 2019-152401 filed Aug. 22, 2019, each of which is hereby incorporated by reference in its entirety.

TECHNICAL FIELD

The present invention relates to a technique to analyze images of a heart and to display analysis results.

BACKGROUND ART

In recent years, the morality rate due to heart diseases has been on the rise, and the necessity of useful and simple diagnostic technology has been highly increasing. MRI diagnostic technology has been making rapid progress, and the importance of MRI has been rising in an image diagnosis of a cardiac region since it is becoming possible to conduct various cardiac examinations in a short time. Regarding "cardiac MRI," examinations such as "cine MRI," "perfusion," "delayed contrast-enhanced method," and "BB (black blood) method" are conducted. Especially, cine MRI that has no limit on the examination range is able to observe arbitrary cross sections and is highly reproducible, compared to an ultrasonic examination, SPECT examination, or the like. Therefore, imaging is performed generally in many medical facilities. As for cine MRI, for example, data collection of "approximately 10 slices/20 phases" is performed for an entire left ventricle by using an electrocardiogram gating method. Recently, a high contrast between blood and myocardium can be obtained by using "Steady State method." Further, in "cardiac function analysis," the necessity of evaluation of cardiac functions by MRI is increasing because accurate values can be obtained as compared with CT, LVG (left ventriculography), and SPECT.

As above, cardiac MRI is clinically useful, and in particular, imaging is performed in cine MRI in many medical facilities, but the images were rarely analyzed by using software. The reason for this is said to be that the software used for conventional cardiac function analysis requires complicated operations to extract and correct the contours of the inner and outer sides of myocardial membranes. Moreover, the reproducibility of the analysis results has also been an issue, since the contour tracing of the inner and outer sides of myocardial membranes is easily influenced by an individual operator. Furthermore, in the situation where cardiac MRI has become more widespread and more medical facilities are using MRI systems provided by multiple manufacturers, the names of the sequences used by each company differ, making it difficult to easily handle the data.

In order to solve the problems above, and to reduce the labor of tracing complicated myocardial contours, software that improves the accuracy thereof and automatically performs processing of interpolation to enable the correction work to be reduced even if an unintended tracing is made, has been provided. In this software, less stressful image observation is enabled by displaying images side by side on the viewer for MRI cardiac function analysis and by flicking operation.

PRIOR ART DOCUMENT

Non-Patent Document

Non-Patent Document 1: https://www.zio.co.jp/ziostation2/

SUMMARY OF THE INVENTION

Problems to be Solved by the Invention

However, it is not easy for a doctor to grasp the pathological condition only by simply displaying MRI images side by side as in the technique described in Non-Patent Document 1. Consequently, it is desirable to display images in accordance with the state of heart. That is, it is desirable to grasp a heart of a human body as a subject, and to display images showing an actual movement, based on a tendency of a change in a waveform or a frequency of a heart, or in an image thereof.

The present invention has been made in view of such a situation and has an object to provide a diagnostic support program capable of displaying a movement of an organ. More specifically, it has an object to generate images that assist a diagnosis by calculating numerical values that assist a diagnosis by digitizing the concordance rate or another non-concordance rate for the waveform and Hz already acquired for new target data to be measured and further by imaging these numerical values.

Means to Solve the Problems (1) In order to achieve the above-described object, the present application has taken steps as follows. That is, a diagnostic support program according to one aspect of the present invention is a diagnostic support program that analyzes images of an organ of a human and displays analysis results, the program causing a computer to execute a process comprising processing of acquiring a plurality of frame images; processing of calculating a cyclic change that characterizes a state of an organ between each of the frame images; processing of Fourier-transforming the cyclic change that characterizes the state of the organ; processing of extracting a spectrum in a fixed band including a spectrum corresponding to a frequency of movement of an organ, out of a spectrum obtained after the Fourier-transforming; processing of performing inverse Fourier transform on the spectrum extracted from the fixed band; and processing of outputting each of the images after performing the inverse Fourier transform.

(2) Further, a diagnostic support program according to one aspect of the present invention has a feature further comprising processing of dividing images of an organ of a human into a plurality of block areas and calculating a change in an image in block areas in each of the frame images; processing of Fourier-transforming the change in an image in each block area in each of the frame images; processing of extracting a spectrum in a fixed band including a spectrum corresponding to a frequency of a movement of an organ, out of a spectrum obtained after the Fourier-transforming; and processing of performing inverse Fourier transform on the spectrum extracted from the fixed band.

(3) Further, a diagnostic support program according to one aspect of the present invention is a diagnostic support program that analyzes images of an organ of a human and displays analysis results, the program causing a computer to execute a process comprising processing of acquiring a plurality of frame images; processing of calculating a cyclic change that characterizes a state of an organ between each of the frame images; processing of calculating a cyclic change that characterizes a state of an organ between each of the frame images; processing of extracting pixels that change corresponding to a frequency of a cyclic change that characterizes the state of the organ in the image by a digital filter; and processing of outputting images including the pixels extracted by the digital filter.

(4) Further, a diagnostic support program according to one aspect of the present invention has a feature further comprising processing of dividing images of an organ into a plurality of block areas and calculating a change in an image in each block area in each of the frame images; and processing of extracting pixels that change corresponding to a frequency of a movement of an organ in the image by a digital filter.

(5) Further, a diagnostic support program according to one aspect of the present invention is a diagnostic support program that analyzes images of an organ of a human and displays analysis results, the program causing a computer to execute a process comprising processing of acquiring a plurality of frame images; processing of calculating a cyclic change rate that characterizes a state of an organ between each of the frame images; processing of selecting a color corresponding to the cyclic change rate that characterizes the state of the organ; and processing of adding the selected color on the change rate of the pixel values and displaying the images on a display.

(6) Further, a diagnostic support program according to one aspect of the present invention has a feature further comprising processing of dividing images of an organ into a plurality of block areas and calculating a change rate in an image in each block area in each of the frame images; and processing of selecting a color corresponding to the change rate of the pixel values for each of the block areas.

(7) Further, a diagnostic support program according to one aspect of the present invention is a diagnostic support program that analyzes images of a human body and displays analysis results, the program causing a computer to execute a process comprising processing of acquiring a plurality of frame images; processing of defining an analysis range for all the acquired frame images; processing of dividing an analysis range into a plurality of areas by using a method of Voronoi tessellation; and processing of executing any of arithmetic operations to be performed on a cyclic change for each of the divided areas.

(8) Further, a diagnostic support program according to one aspect of the present invention is a diagnostic support program that analyzes images of a human body and displays analysis results, the program causing a computer to execute a process comprising processing of acquiring a plurality of frame images; processing of defining an analysis range for all the acquired frame images; processing of dividing an analysis range into a plurality of areas; and processing of classifying each of the areas based on an index of a cyclic change for each of the divided areas.

(9) Further, a diagnostic support program according to one aspect of the present invention is a diagnostic support program that analyzes images of an organ of a human and displays analysis results, the program causing a computer to execute a process comprising processing of acquiring a plurality of frame images; processing of calculating a cyclic change that characterizes a state of an organ in a state where absolute positional relationship of each pixel in a plurality of frame images is maintained; processing of Fourier-transforming the cyclic change that characterizes the state of the organ; processing of extracting a spectrum in a fixed band including a spectrum corresponding to a frequency of a movement of an organ, out of a spectrum obtained after the Fourier-transforming; processing of performing inverse Fourier transform on the spectrum extracted from the fixed band; and processing of outputting each of the images after performing the inverse Fourier transform.

(10) Further, a diagnostic support program according to one aspect of the present invention is a diagnostic support program that analyzes images of an organ of a human and displays analysis results, the program causing a computer to execute a process comprising processing of acquiring a plurality of frame images; processing of calculating a cyclic change that characterizes a state of an organ in a state where absolute positional relationship of each pixel in a plurality of frame images is maintained; processing of extracting pixels that change corresponding to a frequency of a cyclic change that characterizes the state of the organ in the image by a digital filter; and processing of outputting images including the pixels extracted by the digital filter.

(11) Further, a diagnostic support program according to one aspect of the present invention is a diagnostic support program that analyzes images of an organ of a human and displays analysis results, the program causing a computer to execute a process comprising processing of acquiring a plurality of frame images; processing of calculating a cyclic change that characterizes a state of an organ in a state where absolute positional relationship of each pixel in a plurality of frame images is maintained; processing of selecting a color corresponding to the cyclic change rate that characterizes the state of the organ; and processing of adding the selected color on the change rate of the pixel values and displaying the images on a display.

(12) Further, a diagnostic support program according to one aspect of the present invention has a feature of classifying a plurality of frame images into a plurality of groups and calculating a cyclic change that characterizes a state of an organ in a state where absolute positional relationship of each pixel in a plurality of frame images belonging to each group is maintained.

(13) Further, a diagnostic support program according to one aspect of the present invention has a feature of calculating a change in an image in block areas in each of the frame images in a state where relative positional relationship of pixels indicating the organ is maintained between each of the frame images regardless of whether they are adjacent frames or not.

(14) Further, a diagnostic support program according to one aspect of the present invention has a feature further comprising processing of bringing the transmittance changed from transmittance of a specific area in frame images photographed by X-rays, back to an original degree.

(15) Further, a diagnostic support program according to one aspect of the present invention has a feature further comprising processing of correcting a signal value of an area where a magnetic field of MRI is nonuniform in a frame image photographed by MRI and converting it into an image obtained when a magnetic field is uniform.

(16) Further, a diagnostic support program according to one aspect of the present invention has a feature of calculating a change rate from aspects of a change in the entire organ between each of the frame images regardless of whether they are adjacent frames or not, and calculating a change in an image in the specific block areas based on the calculated change rate.

(17) Further, a diagnostic support program according to one aspect of the present invention has a feature that the change rate changes depending on a position of block areas in the organ or is constant throughout the organ.

(18) Further, a diagnostic support program according to one aspect of the present invention has a feature comprising processing of setting a maximum outer edge when the size of the organ is maximum; processing of setting a minimum outer edge when the size of the organ is minimum; processing of calculating coefficients of outer edges of organs of other sizes in each image by using the maximum outer edge and the minimum outer edge; and processing of displaying a waveform corresponding to the coefficients of the outer edges of the organs in each of the images and control points of the waveform on a graph, wherein coefficients of each image are changed by varying positions of the control points.

(19) Further, a diagnostic support program according to one aspect of the present invention has a feature of displaying a pixel average value of the image of the organ on the graph.

(20) Further, a diagnostic support program according to one aspect of the present invention has a feature of displaying the image of the organ juxtaposed with the graph.

(21) Further, a diagnostic support program according to one aspect of the present invention is a diagnostic support program that analyzes images of an organ of a human and displays analysis results, the program causing a computer to execute a process comprising processing of acquiring a plurality of frame images; processing of dividing images of an organ of a human in each of the frame images into a plurality of block areas; processing of calculating a change in an image in block areas in each of the frame images; processing of Fourier-transforming the value of the change in each of the block areas; and processing of classifying each area by colors based on a composition ratio of frequency components.

(22) Further, a diagnostic support program according to one aspect of the present invention is a diagnostic support program that analyzes images of an organ of a human and displays analysis results, the program causing a computer to execute a process comprising processing of acquiring a plurality of frame images; processing of extracting, for each pixel in a specific frame image, pixels having coordinates different from those of each of the pixels in next and subsequent frame images, and calculating a cyclic change that characterizes a state of an organ; processing of Fourier-transforming the cyclic change that characterizes the state of the organ; processing of extracting a spectrum in a fixed band including a spectrum corresponding to a frequency of a movement of an organ, out of a spectrum obtained after the Fourier-transforming; processing of performing inverse Fourier transform on the spectrum extracted from the fixed band; and processing of outputting each of the images after performing the inverse Fourier transform.

(23) Further, a diagnostic support program according to one aspect of the present invention is a diagnostic support program that analyzes images of an organ of a human and displays analysis results, the program causing a computer to execute a process comprising processing of acquiring a plurality of frame images; processing of extracting, for each pixel in a specific frame image, pixels having coordinates different from those of each of the pixels in next and subsequent frame images, and calculating a cyclic change that characterizes a state of an organ; processing of extracting pixels that change corresponding to a frequency of a cyclic change that characterizes the state of the organ in the image by a digital filter; and processing of outputting images including the pixels extracted by the digital filter.

(24) Further, a diagnostic support program according to one aspect of the present invention is a diagnostic support program that analyzes images of an organ of a human and displays analysis results, the program causing a computer to execute a process comprising processing of acquiring a plurality of frame images; processing of extracting, for each pixel in a specific frame image, pixels having coordinates different from those of each of the pixels in next and subsequent frame images, and calculating a cyclic change that characterizes a state of an organ; processing of selecting a color corresponding to the cyclic change rate that characterizes the state of the organ; and processing of adding the selected color on the change rate of the pixel values and displaying the images on a display.

Effect of the Invention

According to one aspect of the present invention, it becomes possible to grasp a heart of a human body as a subject, and to display images each showing an actual movement, based on a tendency of a change in a waveform or a frequency of a heart, or in an image thereof.

DETAILED DESCRIPTION OF EMBODIMENTS

Figure 1:
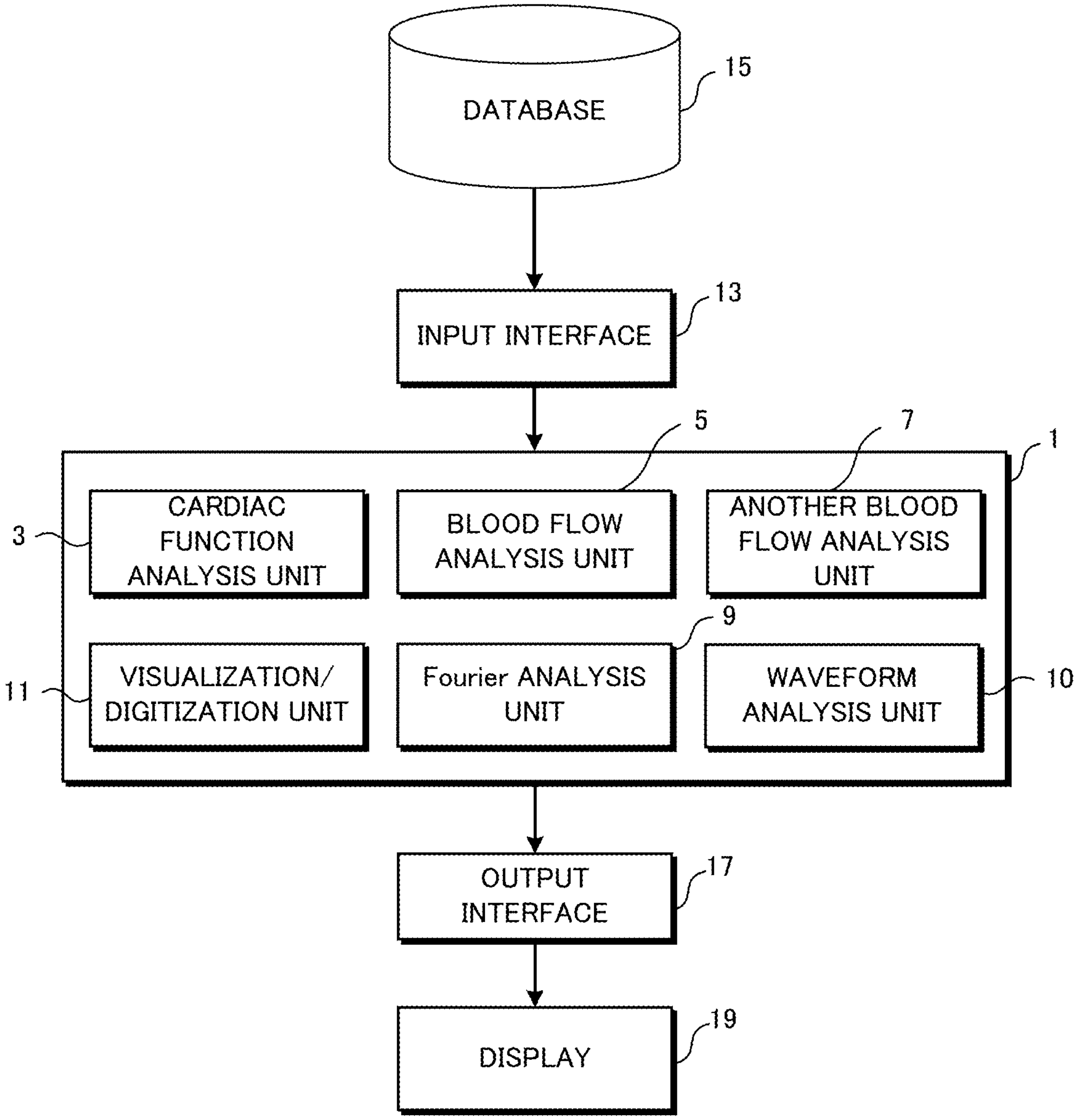
FIG. 1 is a diagram showing an outline configuration of a diagnosis support system according to the present embodiment.

The inventors of the present invention focused on the fact that technology for visualizing a movement of organs (for example, myocardium of a heart) has not been put into practical use conventionally, and found that it becomes possible to support a diagnosis of a doctor by expressing not only deviation of a movement of organs but also places where they are not moving, and came up with the present invention. That is to say, since filtering processing has not been applied well in cardiac image processing technology in the past, the inventors have applied a filter that extracts targeted frequencies to an image of a heart, making what was difficult to see visible. In this way, a diagnosis that required a lot of skill in the past can be simplified, and moving images can be qualitatively represented to give objectivity to displayed contents. Although a heart is used for explanation as an example of an organ in the present specification, it goes without saying that the present invention is not limited to a heart but can be applied to various organs and blood vessels.

In the invention of the present application, assuming that the movement of myocardium is constant, distinguishment is possible by comparison with previous images of a subject, by comparison with a range to be analyzed and entire myocardium averaged, by comparison with normal images, or by comparison with an age sample.

First, the basic concept of the present invention is explained.

According to the present invention, as to a cyclic change that characterizes a state of an organ in a human body, for example, a cross-sectional area, a surface area and volume of a heart, with respect to a movement captured in a repetitive manner in a fixed cycle, a fixed repetition or a fixed movement (routine) on a time axis in the entire or certain partial range is captured as a wave, and measured. For measurement results of the wave, (A) a form of a wave itself or (B) wave intervals (frequency: Hz) is/are used.

As for images of a heart, waves that are linked similarly during the same period of time may exist. For example, in the case of a heartbeat, the following approximation can be conceptualized.

(Average of a change in density in a rough range)≈(a heartbeat)≈(a change in a heart)≈(an electrocardiogram)≈(a change in a surface area and volume of a heart)

In the present invention, for example, with respect to a heart, it is possible to analyze by focusing on deformation of regional ventricular walls (wall thickness dilatation, wall thickness contraction), and it is possible to capture and cyclically represent the systolic thickness, diastolic thickness, and a wall movement (inner and outer membranes). Furthermore, as for a heart, it is possible to capture and cyclically represent "relative wall thickness (RWT)," which is calculated from "(2×posterior wall thickness)/left ventricular end-diastolic diameter)," and "ejection fraction," which is calculated from "(end-diastolic volume−end-systolic volume)/(end-diastolic volume).

In the present invention, it is made to be possible to extract an image with higher accuracy, by using any of these data or data obtained by using those in combination. In this case, calculations may be sometimes interactively carried out many times. At this time, the artifact with respect to the results is eliminated again, and extraction of the function is carried out by extracting from the new data extraction waveform, the data waveform to be the first base, another waveform of modality or the like, the periphery, and the waveform of plural times. In this case, the number of times may be either once or plural times.

Herein, when producing the base data, mutual component extractions are made up for each other by a plurality of modalities (for example, a certain density, a change amount constituted by volumetry, a movement of a heart, and so forth), or by plural times of waveform measurement for a heartbeat and so forth, thereby improving accuracy. By doing this, it becomes possible to reduce the artifact and to improve the accuracy based on a certain fixed prediction of a line or the like.

Here, "density" is translated as "density", but in an image, it means an "absorption value" of pixels in a specific area. For example, in the case of CT, air, bones and water are used as "−1000", "1000", and "0", respectively.

In the present specification, "density" and "intensity" are distinctively used. As described above, "density" means an absorption value and exhibits high air permeability in original images of XP and XP moving images, and air, water and bones are to be displayed as "−1000", "0" and "1000", respectively, by digitizing a portion exhibiting the high permeability as being white. On the other hand, "intensity" is one relatively changed from "density", for example, one displayed via "conversion" into a degree of density and a signal width by being normalized. That is, "intensity" is a relative value of light-dark, an emphasis degree, and so forth. It is represented as "density" or "a change in density (A density)" during directly dealing with the absorption value of an XP image. Then, this is converted thereinto as described above, for image expression reasons, and represented as "intensity". For example, "intensity" is given in a case where color displaying to 256-step gray scales of from 0 to 255 is carried out. Such a terminology distinction is applicable to the case of XP or CT.

On the other hand, in the case of MRI, even though air, water and bones are attempted to be set as "−1000", "0" and "1000", respectively, there is a situation in which the values are largely changed due to pixel values of MRI, types of measuring machines, a person's physical conditions at the time of measurement, build of a body, and measuring time; and how to acquire signals of MRI such as T1 emphasis images and so forth also varies by a facility thereof and the types of measuring machines, thereby being unable to be fixed. Accordingly, in the case of MRI, no definition of “density” can be applied thereto as with the case of XP and CT. Therefore, MRI deals with relative values from a stage of initial extraction, thereby expressing as “intensity” from the beginning. Then, the signals for processing are also “intensity”.

From those described above, it becomes possible to obtain master data. For the above-described master data, a new target desired to be measured is extracted in a certain fixed width and range of a waveform and Hz of a wave of the above-described master data. For example, extraction is performed only for a heartbeat, or in the width or range as a frame of a degree of blood vessel extraction. In addition, this waveform and the width of Hz are relatively and collectively determined based on statistics by using the waveform element in another function, artifacts such as noise and so forth, the waveform of another modality deemed to have another tunability, reproducibility performed plural times, and so forth. Then, adjustment and experience are required therein (it is also possible to apply machine learning thereto). This is because while the width and range are extended, the element of another function begins to enter, and if they are too narrow, the element of the function itself is eliminated, and thus the range needs to be adjusted. For example, in the case of presence of data of plural times, it is easy to specify the range, Hz, the concordance width in measurement, and so forth. Further, fluctuations in axis, width, range, and Hz due to the mutual component extractions and the width can be estimated. That is, by plural times of superimposition, the axis setting of Hz is averaged and the optimum range of each of the axis, width, range, and Hz is calculated via variance. At this time, there is a case where Hz (noise) of another behavior is extracted, and if a wave thereof exists, the degree in which no wave is included in the case of presence of the wave is also relatively measured.

Next, for the new target data to be measured, a concordance rate and other non-concordance rates with already captured wave shape and Hz are quantified to calculate numerical values that assist a diagnosis. For example, it can be applied to a diagnostic assist instrument by measuring a waveform concordance rate of disease of a master and calculating the disease waveform concordance rate along with noise exclusion of a pulsimeter or auscultation. In the present specification, a case where a tunable concordance rate can be used is explained.

[With Regard to a Tunable Concordance Rate]

In the present specification, a tendency of an image change is explained as a tunable concordance rate. For example, a myocardial area is detected and divided into a plurality of block areas to calculate average density (pixel value x) of the block areas in each frame image. Then, a ratio (x') of an average pixel value of block areas in each frame image to a change width (0% to 100%) from the minimum value to the maximum value of average density (pixel value x) is calculated. On the other hand, by using a ratio value (x'/y') of a ratio (y') of a change (y) in myocardium of each frame image to a change width (0% to 100%) from at the minimum position to at the maximum position of the myocardium, only block areas for which the ratio value (x'/y') is within a predetermined fixed range are extracted.

Herein, the case where y'=x' or y=ax (a represents a numerical value of an amplitude of myocardium, or a coefficient of a numerical value of density) means complete concordance. However, it does not mean that only the case of the complete concordance indicates a meaningful value, and a value having a certain fixed width should be extracted. Thus, according to one aspect of the present embodiment, a fixed width is determined using logarithms (log), as described below. That is, when calculated at a ratio (%) in the case where y=x, complete concordance of tunability is “log Y'/x'=0”. Further, when extracting one in which a range of a tunable concordance rate is narrow or a (numerically narrow) range, for example, it is determined as “log Y'/x'=−0.05~+0.05” in the range that is close to 0, and when being one in which a range of a tunable concordance rate is wide or a (numerically wide) range, for example, it is determined as “log Y'/x'=−0.5~+0.5” in the range that is close to 0. As this range is narrower, and the numerical value that is concordant within the range is also higher, the tunable rate can be said to be higher. When counting the number by determining this ratio value for each pixel of the pixels, a normal distribution in which the case of complete concordance is taken as a peak is obtained in the case of healthy persons. In contrast, in the case of those having disease, a distribution of this ratio value is to be lost. In addition, as described above, the method of determining a width using logarithms is only one example, and the present invention is not limited thereto.

That is, the present invention is one performing “image extraction” as the following: (average of a change in density in a rough range)≈(a heartbeat)≈(a change in a heart)≈(an electrocardiogram) (a change in a surface area and volume of a heart), and is also applicable to methods other than the method of using logarithms. It becomes possible to display a frequency tunable image via such a method.

In the case of blood vessels, as to a series of changes of density (x (one waveform at a pulmonary hilum portion) produced by responding to a series of contractions of a heart (y), a slight time delay (a change in phase) is, as is, present, thereby being displayed as y=a'(x−t). In the case of complete concordance, since t=0, y=x or y=a'x. Here, when extracting one in which a range of a tunable concordance rate is narrow or a (numerically narrow) range, for example, it is determined as “log Y'/x'=−0.05~+0.05” in the range that is close to 0, and when being one in which a range of a tunable concordance rate is wide or a (numerically wide) range, for example, it is determined as “log Y'/x'=−0.5~+0.5” in the range that is close to 0. As this range is narrower, and the numerical value that is concordant within the range is also higher, the tunable rate can be said to be higher.

In the case of other blood vessels, the above-described “portion responding to a heart” is excluded, and density on the center side that is plotted from pulmonary hilum can be used. The case of peripheral blood vessels may be also similarly taken care of.

Further, the present invention may also be applied to a circulatory system. For example, a change in density of a heart is directly associated with a change in density of a blood flow to a pulmonary hilum portion—a peripheral lung field, and a change in a series of changes in density of the heart and a change in density of the pulmonary hilum portion are subjected to a type of conversion, and transmitted, as is, thereto. It appears that this is produced by obtaining a slight phase difference from the relationship between the change in density of the heart and the change in density of the pulmonary hilum portion. Further, a change in density of the pulmonary hilum portion or the like is associated, as is, with a change in density of a lung field to a blood flow, and thus it is possible to express tunability by one (concordance rate relationship in Y X) reflected with an as-is rate. Further, it appears that as to a cervical blood vessel system, a change in density plotted at central heart blood vessels on the periphery thereof is directly associated therewith, or also associated therewith accompanying a slight phase in a similar manner. Then, when the density varies depending on the background, and is propagated, it becomes possible to be considered as a tunable concordance rate so as to propagate the situation of a change in density.

Herein, regarding each of a change amount in one image and a change rate in one image, for being displayed as a relative value (Standard Differential Signal Density/Intensity) when a change amount from density of a heart is set to 1, the change amount and the change rate can be extracted for each of (1) as to a different image for each image, an image when 1 is set to each one (general assumption), (2) as to a different image for each one, a ratio when the a heartbeat obtained by adding density (a change amount and a change rate) thereto is set to 1, and (3) as to carrying out photographing plural times, the ratio obtained as a total amount of density while taking each respiration that is set to 1.

Further, in the case of 3D of MR or the like, as to a value (when it is set to 1 at this time) obtained by summing intensity (in the case of MR) or density (in the case of CT) of a heartbeat, the difference of its intensity or density can be converted into "peak flow volume data" of the heartbeat (during rest, or even during a load), and as to this value, an actual measurement amount of movement and a movement rate of a heart can be converted thereinto by finding a ratio of intensity or density when calculating "3D×time" with at least MRI, CT or the like. Similarly, it becomes possible that a distribution in "capillary phase" of "flow" in a lung field presents an estimation value of being converted into a distribution of a lung blood flow peripheral amount, or volume by inputting one time cardiac output.

That is, (Average of a change in density in a rough range)≈(a heartbeat)≈(a change in a heart) (an electrocardiogram) (a change in a surface area and volume of a heart) is satisfied, and when taking out only a change amount of one with 10% or 20%, an estimation value is possible to be calculated by calculating (the whole number of those)×(a change amount in that time).

Then, for the new target data to be measured, images that assist a diagnosis are calculated, by imaging the concordance rate or another non-concordance rate for the waveform and Hz already captured. For example, the differences between normal swallowing and a patient's swallowing are visualized, and the differences between movements that the patient has been making so far and movements that the patient is currently making are shown. For example, changes and differences in the way of walking and in swinging are included.

The extracted change amount is visualized and extracted onto an image. This is cardiac function analysis and blood vessel (a blood flow) analysis as explained below. Then, a change rate of myocardium is visualized. At this time, there are some cases where the artifact with respect to the results is eliminated again and extraction of the function is carried out by extracting from the new data extraction waveform, the data waveform to be the first base, another waveform of modality or the like, the periphery, and the waveform of plural times. The method of eliminating the artifact is described later.

Further, there is a case where the feature amount is grasped even from those from which change components extracted from other than those extracted as described above are excluded. For example, when grasping a movement of the abdominal intestinal tract, an attempt is made to extract the movement of the abdominal intestinal tract by excluding the influence of respiration and the influence of blood vessels from the abdomen.

Further, based on the change rate due to the extraction, correction is applied to images that take a certain fixed amount of photographing time (CT, MRI, special radiography, PET/scintigraphy, and the like) to provide clearer and more accurate images. For example, it is useful for ascending aorta cardiac correction, cardiac morphology correction, correction of bronchial blurring, evaluation of the periphery of a thorax, and imaging when the patient is unable to hold his or her breath (which may take several minutes to photograph).

Hereinafter, an embodiment of the present invention is explained referring to the drawings. FIG. 1 is a diagram showing an outline configuration of a diagnosis support system according to the present embodiment. This diagnosis support system performs a specific function by causing a computer to execute a diagnostic support program. A basic module 1 includes a cardiac function analysis unit 3, a blood flow analysis unit 5, another blood flow analysis unit 7, a Fourier analysis unit 9, a waveform analysis unit 10, and a visualization/digitization unit 11. The basic module 1 acquires image data from a database 15 via an input interface 13. The database 15 stores, for example, images via DICOM (Digital Imaging and Communication in Medicine). An image signal output from the basic module 1 is displayed on a display 19 via an output interface 17. Next, the function of the basic module according to the present embodiment is explained. Furthermore, the input images are not limited to the database 15, but can also be input from other external devices via the input interface 13 or by initiative.

[Refinement of Detecting a Dynamic Region]

There is a case where contrast in a dynamic region such as a lung field, a thorax, and a heart is not uniform along a line. In this case, a shape of the dynamic region can be more precisely detected by changing a threshold used for eliminating noise, and performing processing of detection plural times. For example, as for a left lung, the contrast on the line of the diaphragm tends to be weaker toward the inside of a human body. There is also a circumstance that the cardiac apex part and the cardiac base part have smaller movements and the central part of the heart has a bigger movement. In this case, the remaining part of the left half of the diaphragm, the parts where the movement of the heart is big and the parts where the movement of the heart is small can also be detected by changing setting of the threshold used for eliminating the noise, or by multiplying the pixel value by a different factor. It becomes possible to detect a shape of the entire diaphragm or to detect a shape of the entire heart by repeating this processing plural times. In this manner, the present method also enables digitizing not only the position of the diaphragm but also a change rate and a change amount of a line and a surface concerning a shape of a thorax, a heart, and a dynamic region, and it can be used for a new diagnosis.

In this way, it becomes possible to utilize the position or shape of diaphragm and a heart detected in a diagnosis. That is, it is possible to graph coordinates of diaphragm and a heart; to calculate coordinates of a thorax, diaphragm, and a heart using curves (surfaces) or straight lines calculated as described above; and to graph a heartbeat, a blood vessel beat, "density" in a lung field and so forth as a position corresponding to a cycle, or coordinates. Such a method is applicable to a dynamic region linked with respiration and cardiac pulsation.

When not only Hz in each of expired air, inspired air, a systole, and a diastole, but also a frequency (Hz) of a dynamic region linked with diaphragm or respiration or a frequency (Hz) of a dynamic region of a heart is changed, such a method enables measurement in a frequency band responding to the change. Then, during spectrum extraction of BPF (band pass filter), in a fixed range, it becomes possible that BBF is set depending on each respective state of respiration or a heart; that an optimal state can be caused by variation of an axis at the BPF position in each "reconstruction phase" of respiration or a heart; and that BPF in variability accompanying the foregoing is prepared. Even if a respiratory rhythm varies such as when breathing slow or stopping breathing (Hz=0), or even if temporary fibrillation of the heart (an extreme high frequency) or stopping breathing (Hz=0) appears, this enables providing images according to the foregoing.

Further, a frequency of the whole expired air or inspired air may be made to be calculated based on a ratio of a respiratory element (a respiratory element including all or part of expired air or inspired air) to the whole expired air or inspired air. Similarly, a systole or a diastole, a frequency element, and other whole frequencies may be made to be calculated based on a ratio of a cardiac dynamic element (a cardiac dynamic element including all or part of the systole or diastole) to a cardiac systole and diastole, one pulsation of a heart, and pulsations of the whole measurement. In addition, those for which detecting of diaphragm and a heart is carried out plural times, and a signal and a waveform thereof are stable may be made to be selected. Accordingly, it becomes possible to calculate at least one frequency of a respiratory element and a cardiac pulsation element from a position or shape of the detected diaphragm, or a position or shape of the dynamic region linked with a respiration, and to calculate a frequency that represents the heartbeat. In becomes possible to grasp the frequency and the heartbeat of the respiratory element and the cardiac pulsation element when the position or shape of the diaphragm and the heart or the dynamic region are/is able to be grasped. This method enables tracking the subsequent waveform even though dividing a part of the waveform. Thus, it is possible to follow the original respiratory element or cardiac pulsation element even though the frequency of the respiratory element or cardiac pulsation element changes on the way. Further, pulsation of a heart and so forth often undergo a sudden change, but the same thing is also possible to be applied to cardiac blood vessels and organs related to cardiac blood vessel waveforms.

[Detection of Lung Fields]

Figure 11:
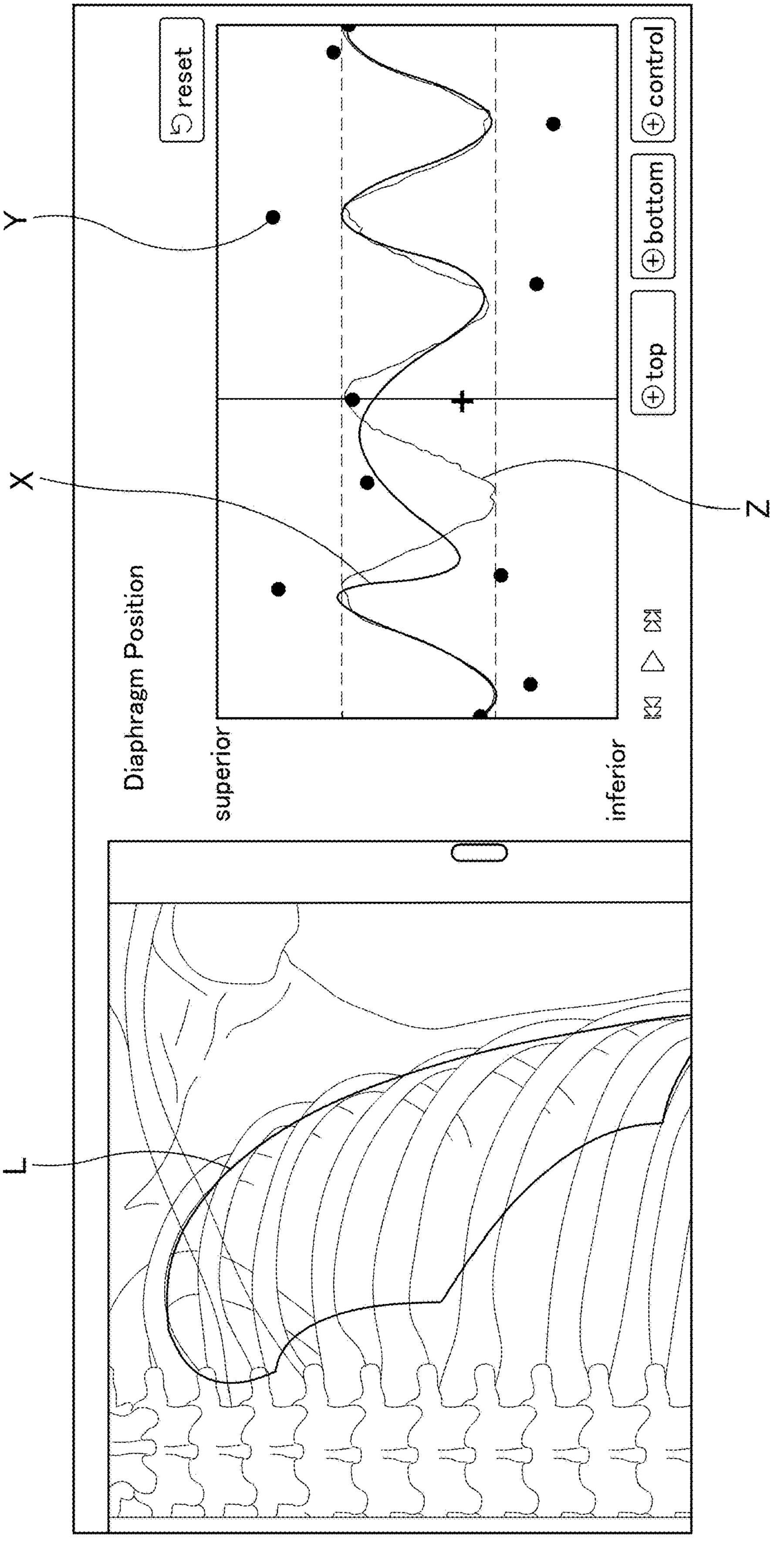
FIG. 11 is a diagram showing an example of a method of detecting a lung field in the present invention.

In the present invention, it is possible to refine detection of lung fields as one aspect of the above-described "refinement of detecting a dynamic region." In this processing, after setting the maximum and minimum lung fields, the other lung fields are calculated using the values. FIG. 11 is a diagram showing an example of a lung field detection method in the present invention. In this method, the "B-spline curve" is used to represent the "coefficient of each image." In FIG. 11, the waveform X represents the "coefficient of each image L showing the lung field," and from the left to right direction, the coefficient of the first image, the coefficient of the second image . . . and so on, are shown. The "coefficient of each image" changes smoothly when the control point Y in FIG. 11 is moved. In the present invention, in this way, the graph of the coefficients can be edited directly. In FIG. 11, the "gray polygonal line Z" represents the "pixel average value of each image." When photographing under optimal conditions, the change in the size of the lung field coincides with the change in the pixel average value. Herein, this pixel average value can be smoothed by curve fitting and directly used as a "coefficient." The same method can be applied to a heart and other organs involved in a cardiovascular frequency.

[Cardiac Function Analysis]

FIG. 2 is a cross-sectional view showing an outline structure of a heart. The "cardiac function" is generally defined as "the pumping function of the left ventricle, which circulates blood through the body." Cardiac function analysis is important for estimating the prognosis of patients with "ischemic heart disease," especially "myocardial infarction." For example, if the value of the left ventricular ejection fraction (EF) decreases, the heart's output as a pump decreases and it becomes unable to pump enough blood throughout the body. Other cardiac functions include left ventricular end-diastolic volume (EDV), left ventricular end-systolic volume (ESV), stroke volume (SV), cardiac output (CO), and a cardiac index (CI). For local evaluation of myocardium, "Bull's eye map" is used, which shows wall thickness, a wall movement, a change rate of wall thickness, and the like, as shown in FIGS. 2B and 2C, which are cross-sections in planes perpendicular to the axis A in FIG. 2A. This "Bull's eye map" is an image displayed with the cross-section of the apex placed in the center of the circle, and the short-axis tomographic images arranged in concentric circles outside thereof, with the cross-section of the heart base at the outermost position.

According to the present embodiment, in addition to the "Bull's eye map" being used, the cycle of a movement of a heart is analyzed based on the following indexes. That is, a cycle of a movement of a heart is analyzed by using density/intensity in a fixed area inside a cardiac region. Further, a range constituted by certain fixed volume density/intensity measured in a region exhibiting high permeability of X-ray (besides that, a plurality of kinds of modality such as others including CT and MRI), data obtained by another measurement method such as spirogram or the like, and external input information, may also be used. In addition, it is desirable to compare the analysis results for each heartbeat and analyze the tendency from a plurality of pieces of data to improve the accuracy of the data. Also, it is possible to identify the edge of a heart and obtain a frequency based on a change in this edge of the heart. Further, it is possible to identify the border of a lung field and obtain a frequency from the movement of the border.

[Blood Vessel Beat Analysis]

According to the present embodiment, the blood vessel beat is analyzed based on the following indexes. That is, the blood vessel beat is analyzed using a change in density/intensity of each region by specifying the heart/position of pulmonary hilum/main blood vessel from the measurement results of other modalities such as an electrocardiogram and a pulsimeter, or from the lung contour. Further, a change in density/intensity of a target region may be analyzed by manually performing plotting on an image. Then, it is also possible to use the heartbeat element obtained from a heartbeat or a blood vessel beat. In addition, it is desirable to improve accuracy of data by comparing the analysis results for each beat and analyzing the tendency from a plurality of pieces of data. Further, it becomes possible to improve accuracy by performing the extraction of density/intensity of each region plural times, as well as by performing the foregoing with respect to a fixed range. Further, there is also a method of inputting a cardiovascular beat frequency or a frequency band.

[Identification of a Cardiac Region]

An image is extracted from the database (DICOM), and a cardiac region (especially myocardium) is automatically detected by using results of the cardiac function analysis as described above. Next, the myocardium is divided into a plurality of block areas to calculate a change in each block area. Herein, size of the block area may be determined depending on a photographing speed. When the photographing speed is slow, the corresponding region is difficult to be specified on a frame image behind a certain frame image, and thus the block area is made to be large. On the other hand, when the photographing speed is fast, the number of frame images per unit time is large, and thus, it is made to become possible to follow even when the block area is small. Further, the size of the block area may be calculated depending on which timing out of a cycle of the cardiac movement is selected. Herein, it is often necessary to correct deviation of the myocardial region. In this case, the cardiac movement is identified, and the relative position of the cardiac contour is further grasped to relatively make evaluations based on the movement. In addition, when the block area is too small, a flicker often occurs in the image. In order to prevent this, the block area needs to have a fixed size.

[Preparation of Block Areas]

Figure 2A:
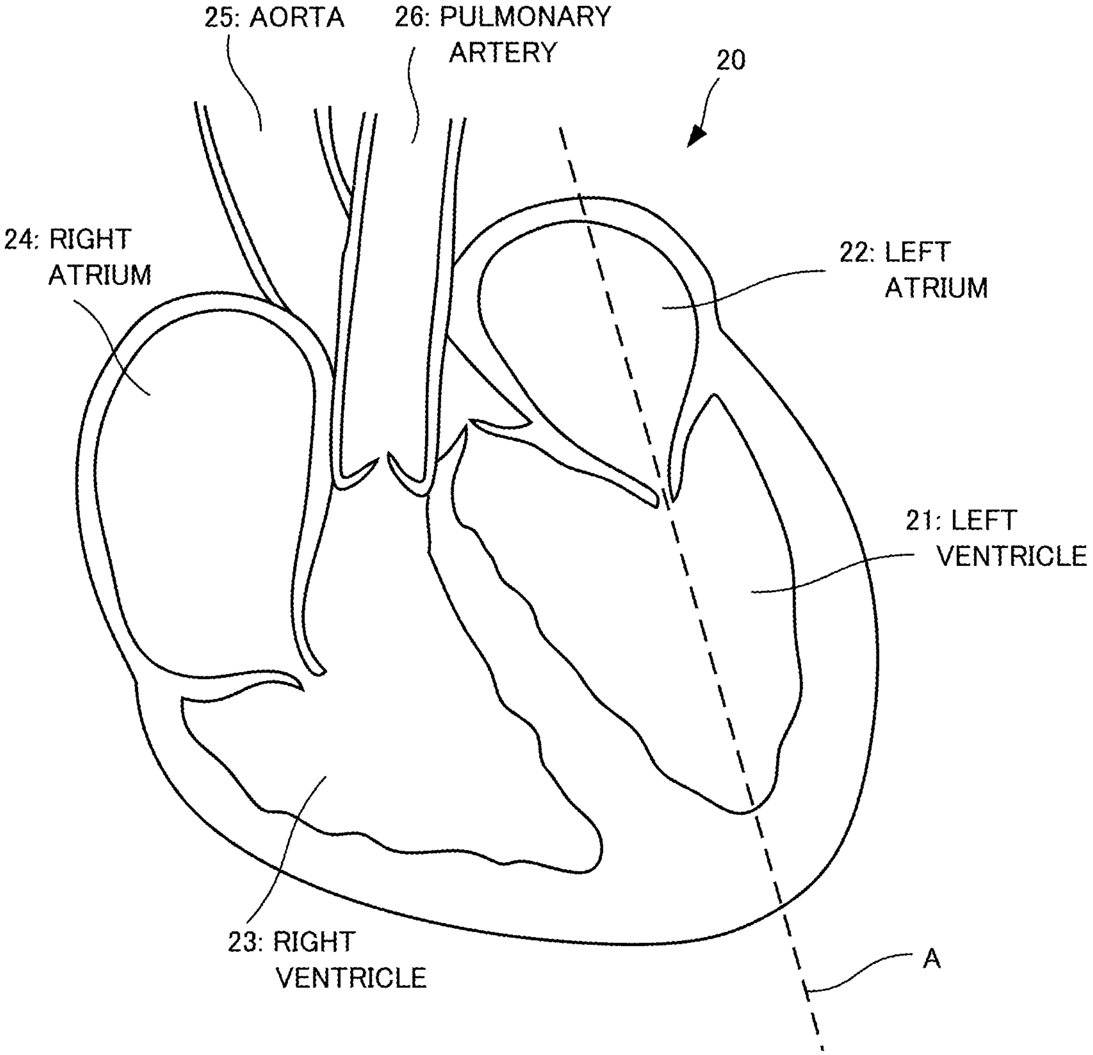
FIG. 2A is a diagram showing a sectional view of a heart.
Figure 2B:
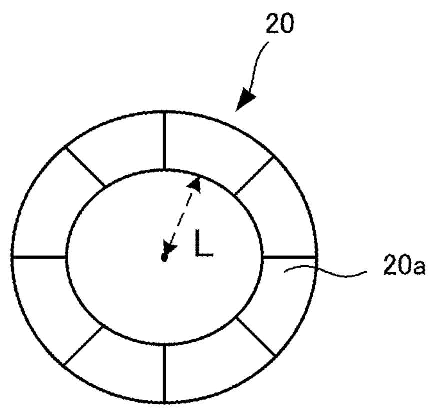
FIG. 2B is a diagram showing a sectional view of a heart.
Figure 2C:
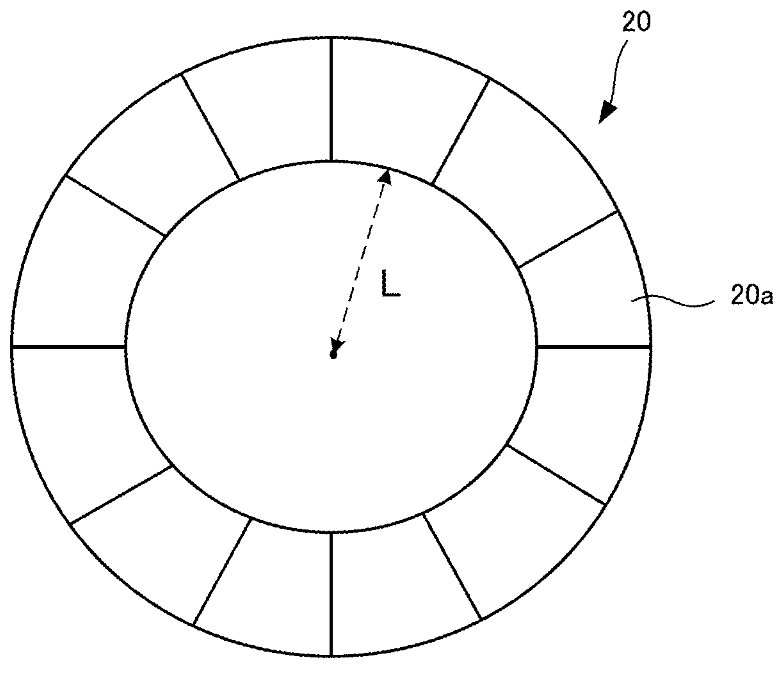
FIG. 2C is a diagram showing a sectional view of a heart.

Next, a method of dividing myocardium into a plurality of block areas is explained. FIGS. 2B and 2C are diagrams showing a method of dividing myocardium radially from the center of the heart. As to the cardiac region, the movement of the heart and the position relationship of blood vessels are identified and the relative position of the cardiac contour is grasped, and the evaluation should be relatively made based on the movement. Thus, in the invention of the present application, after automatically detecting a cardiac contour, a myocardial region is divided into a plurality of block areas to average the value (pixel value) of a change of an image included in each block area. As a result of this, even though a form of a heart changes over time, it becomes possible to track changes of the region of interest with the lapse of time.

On the other hand, when being divided into block areas without specifying a cardiac region, due to a change of the heart with the lapse of time, the region of interest falls outside the cardiac region, thereby resulting in a meaningless image. Further, there is a method of inputting a heartbeat or a frequency band. Further, these methods are also applicable to three-dimensional stereoscopic images. By keeping the pixels in three-dimensional stereoscopic images constant, calculation can be made for region dividing in three-dimensional stereoscopic images. Such relative evaluation based on the movement of relative positions can be performed between adjacent frame images, or can be performed for every integer multiple of images, such as every two images or every three images. In addition, several images can be grouped together and processed for each group.

Figure 7A:
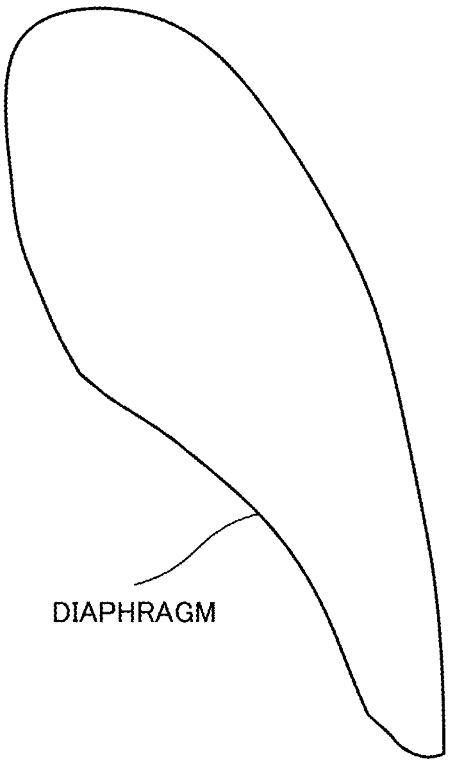
FIG. 7A is a schematic diagram showing a left lung of a human body from the front.
Figure 7B:
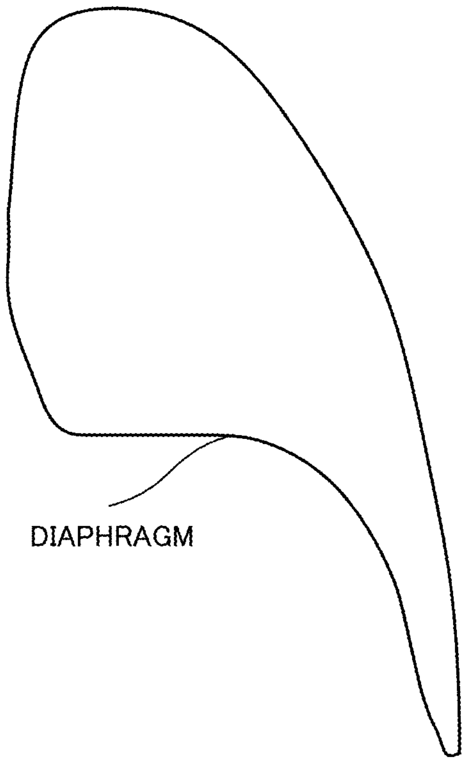
FIG. 7B is a schematic diagram showing a left lung of a human body from the left side.
Figure 8A:
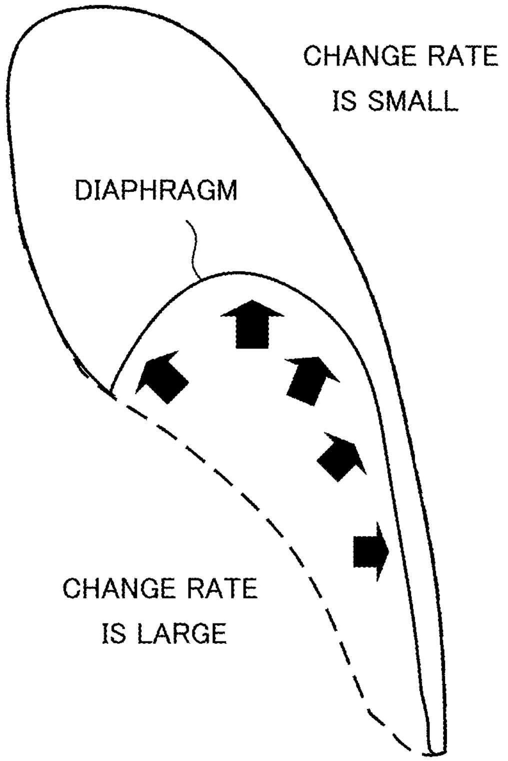
FIG. 8A is a schematic diagram showing a left lung of a human body from the front.
Figure 8B:
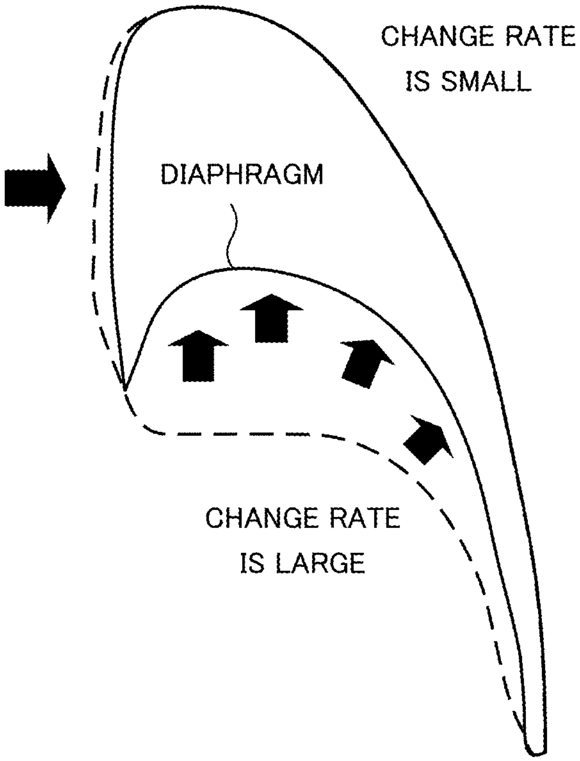
FIG. 8B is a schematic diagram showing a left lung of a human body from the left side.

FIG. 7A is a schematic diagram showing a left lung of a human body from the front, and FIG. 7B is a schematic diagram showing a left lung of a human body from the left side. FIGS. 7A and 7B both show the inspiration, namely, a lung in the state of breathing in. FIG. 8A is a schematic diagram showing a left lung of a human body from the front, and FIG. 8B is a schematic diagram showing a left lung of a human body from the left side. FIGS. 8A and 8B both show the expiration, namely, a lung in a state of breathing out. As shown in these figures, the form of a lung field changes greatly during respiration, but the change rate in the lung field on the side of the diaphragm is large, while the change rate in the lung field on the opposite side of the diaphragm is small. In the present invention, the position of each region in the lung field is changed depending on this change rate. This enables performing relative evaluation based on the relative positional relationship of each region within the lung field region. In addition, based on the change rate in the lung field (for example, the average change rate), the relative positional relationship can be represented by a constant change rate in the lung field region, or the change rate can be adaptively varied in the lung field region depending on the distance from the diaphragm. In this way, by using the variation rate in the lung field region, it becomes possible to display an image that is synchronized with the respiratory cycle.

Figure 9A:
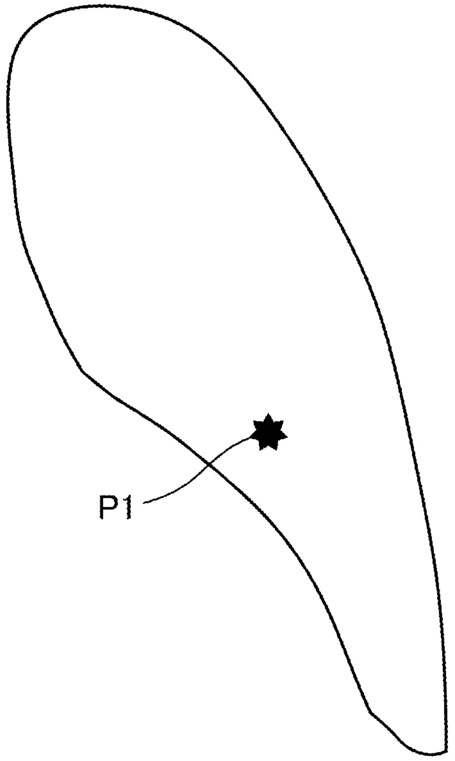
FIG. 9A is a schematic diagram showing a left lung of a human body from the front.
Figure 9B:
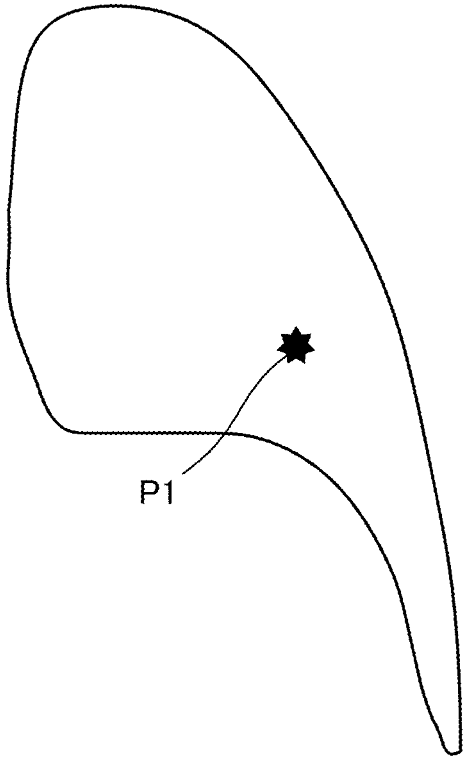
FIG. 9B is a schematic diagram showing a left lung of a human body from the left side.
Figure 10A:
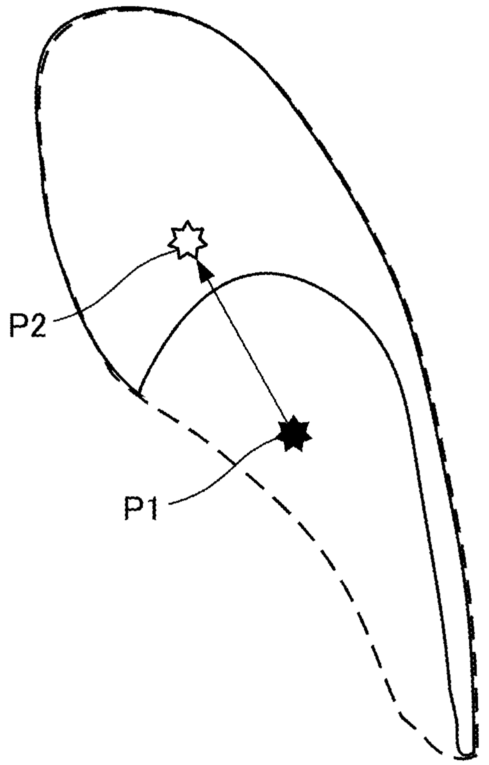
FIG. 10A is a schematic diagram showing a left lung of a human body from the front.
Figure 10B:
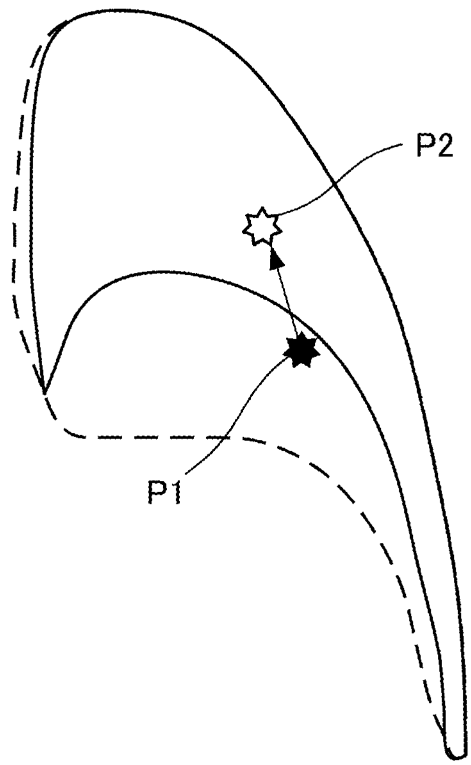
FIG. 10B is a schematic diagram showing a left lung of a human body from the left side.

FIG. 9A is a schematic diagram showing a left lung of a human body from the front, and FIG. 9B is a schematic diagram showing a left lung of a human body from the left side. FIGS. 9A and 9B both show the inspiration, namely, a lung in the state of breathing in. FIG. 10A is a schematic diagram showing a left lung of a human body from the front, and FIG. 10B is a schematic diagram showing a left lung of a human body from the left side. FIGS. 10A and 10B both show the expiration, namely, a lung in a state of breathing out. For example, as shown in FIGS. 9A and 9B, marker P1 is plotted at a position in the lung field region in a state of inspiration. Assuming that marker P1 is a fixed point defined by two-dimensional coordinates, the coordinates remain the same even in a state of expiration, so marker P1 exist in the same position, as shown in FIGS. 10A and 10B. On the other hand, in the present invention, as described above, evaluation is performed in terms of the relative positional relationship to the entire lung field region, so in a state of expiration, the point moves to the position of marker P2 instead of the position of marker P1. It is also possible to use the vector at this time to evaluate the point plotted during inspiration and the point identified to move to during expiration.

Figure 2D:
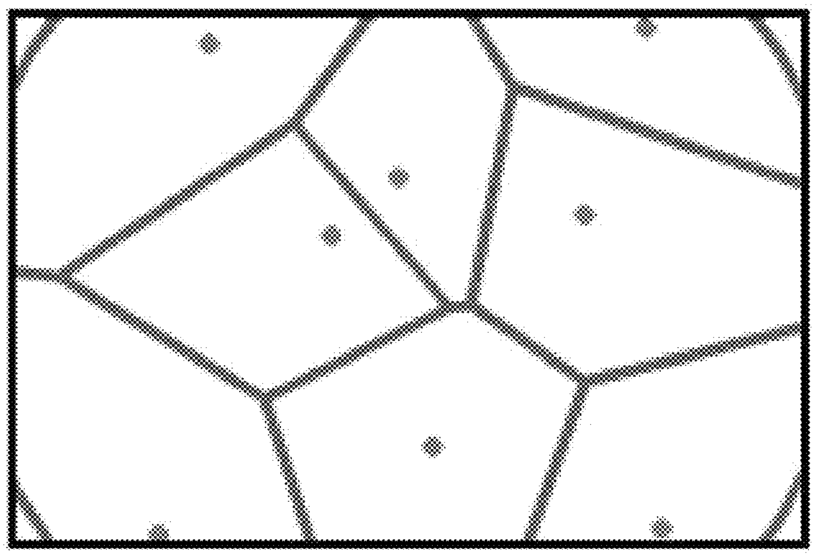
FIG. 2D is a diagram showing an example of Voronoi tessellation.

To divide a region, Voronoi tessellation (Thiessen tessellation) can be applied. The Voronoi tessellation is, as shown in FIG. 2D, a "method of drawing perpendicular bisectors on the straight line connecting neighboring base points and dividing the nearest neighbor region of each base point." By applying such Voronoi tessellation, it becomes possible to shorten the calculation time. Furthermore, when drawing a straight line connecting neighboring base points, weighting may be applied depending on the analysis target. For example, when dividing the region of the pulmonary arteries, the weighting may be increased for thicker region and the weighting may be decreased for thinner region. This enables dividing depending on the analysis target while reducing the burden in processing. In addition, as for a plurality of block areas appeared due to the division, classification processing may be performed based on indicators such as a change in pixel values (a cyclic change).

In this way, after dividing a region to a plurality of block areas, a change in an image in each block area is calculated based on the relative position of each block area to a dynamic region such as a heart. Herein, not only the range of the mass itself as a pixel is taken as a unit got the difference of signals, but also the difference of signals can be taken in a range smaller than the mass, or in a larger range that surrounds the mass. Further, it is also possible to increase the range in the vertical direction only in the vicinity of the diaphragm, increase the range in the horizontal direction only in other dynamic regions, deform the shape of the range, or connect the regions of pixels. In addition, after calculating one or more differences, it is desirable to define the form of the mass again to match the form of the entire lung field and heart. For example, after processing is performed from the first image to the second image, the form of the mass can be created again in the second image to match the shape and then compared to the second image to the third image.

In the description above, the "relative positional relationship" in consideration of an organ movement is described, but the present invention is not limited to this and it is also possible to perform image processing while maintaining "absolute positional relationship of each pixel" in a plurality of frame images. The "absolute positional relationship of each pixel" refers to the relationship between pixels whose coordinates are specified based on the two-dimensional coordinate axis when the two-dimensional coordinate axis is defined on the frame image. In other words, it is a method of pixel processing in which the pixel of interest is invariant. The processing of maintaining the "absolute positional relationship of each pixel" assumes a plurality of frame images, but the number of frame images is not specified. A plurality of frame images can be classified into a plurality of groups, and each group can include the equal number of frame images, or each group can include the different number of frame images.

That is to say, in a state where a plurality of frame images is classified into a plurality of groups and the absolute positional relationship of each pixel in a plurality of frame images belonging to each group is maintained, the change in the pixel value of the organ, the change in the distance from the center to the outer edge of the organ, or the change in the volume of the organ is calculated. This enables handling a pixel value as an equal one even if it changes slightly, thereby reducing the amount of the data and processing steps.

Further, positional relationship that is neither relative positional relationship nor absolute positional relationship can be conceived. This means that, point P having specific coordinates in a particular frame image can be defined and another point Q having different coordinates from the above specific point can be defined in the next and subsequent frame images, but in this case, the size of vector PQ is assumed to be small in relation to the movement of the organ. Further, for point Q, other point R having slightly different coordinates than point Q is defined in the next and subsequent frames. By repeating this operation, other point with slight deviation from a specific point P is extracted for each frame image, and the present embodiment is applied. Specifically, a plurality of frame images is acquired, and for each pixel in a specific frame image, pixels having different coordinates from each of the pixels in the next and subsequent frame images is extracted, and a cyclic change that characterizes the state of the organ is calculated.

Then, Fourier-transforming is performed on the cyclic change that characterizes the state of the organ, a spectrum in a fixed band including a spectrum corresponding to a frequency of a movement of an organ out of a spectrum obtained after the Fourier-transforming is extracted, inverse Fourier transform is performed on the spectrum extracted from the fixed band, and each of the images after performing the inverse Fourier transform is output. Further, pixels that change corresponding to a frequency of a cyclic change that characterizes the state of the organ in the image may be extracted by a digital filter, and images including the pixels extracted by the digital filter may be output. Also, a color corresponding to the cyclic change rate that characterizes the state of the organ may be selected, and the selected color may be added on the change rate of the pixel values and the images may be displayed on a display. This enables expressing the movement of the organ.

Next, artifacts are eliminated to interpolate the image data. That is, when bones or the like are included within the analysis range, they represented as noise, and thus, it is desirable to remove the noise therefrom by using a noise-cut filter. As for X-ray images, conventionally, air and bones are set as −1000 and 1000, respectively, and thus a high permeability portion exhibits a low pixel value and is displayed black, and a low permeability portion exhibits a high pixel value and is displayed white. For example, when displaying the pixel value by 256 gradations, black becomes 0, and white becomes 255.

Within a cardiac region, X-rays hardly transmit the position where blood vessels and bones are present, and thus the pixel value of an X-ray image becomes high and the X-ray image becomes white. The same thing can also be applied to other CT and MRI. Herein, from the results obtained by the above-described cardiac function analysis, it becomes possible to eliminate artifacts by interpolating data by using values in the same phase, based on a waveform per heartbeat. Further, when detecting that "coordinates are different therefrom", "the pixel value extremely varies", or "a frequency and density abnormally become high", cut-off is carried out for these, and with respect to the remaining obtained images, this may be easily used for Hz calculation of the heart and adjustment of the myocardial region, for example, by identifying the continuously smooth waveform using a least squares method and so forth. Further, when superimposing an image thereon, there are (1) the case where acquired comparison images obtained by acquiring each image before and after are superimposed with the coordinates themselves, and (2) a method of superimposing relative position information on a base by relatively extending images, after acquiring each image before and after to the base. By using the methods as described above, it becomes possible to correct a form of a cardiac region and to correct changes in images in block areas.

Herein, "reconstruction" in the time axis is explained. For example, when inspiration time of 15 f/s is 2 seconds, 30+1 images are obtained. In this case, the "reconstruction" for each 10% can be carried out if 3 images are simply superimposed at each time. At this time, for example, when 0.1 seconds indicate 10%, and in the case where the image acquires only a photograph of each of 0.07 seconds and 0.12 seconds, "reconstruction" of 0.1 seconds is needed. In this case, an intermediate value in images of before or after 10%, a (an average value of both) value, is given to carry out "reconstruction". Further, the time axis is taken, and the coefficient may be changed at a ratio of the time. For example, when there is no photographing value of 0.1 seconds due to the presence of the time axis difference, and there is a photographing time of each of 0.07 seconds and 0.12 seconds, "recalculation" is made as "(a value of 0.07 seconds thereof)$\times\frac{2}{5}$+(a value of 0.12 seconds)$\times\frac{3}{5}$" to perform "reconstruction". In addition, it is desirable to include 0 to 100% of "Maximum Differential Intensity Projection", and to perform calculation by providing ranges such as "reconstruction" of 10 to 20%, "reconstruction" of 10 to 40%, and so forth. In this manner, it is also possible to carry out "reconstruction" at a ratio of one heartbeat for the unphotographed portion. In addition, according to the present invention, it is also possible to carry out "reconstruction" similarly to a heart, a blood flow, and a series of movements linked with those other than these.

[Fourier Analysis]

Figure 3A:
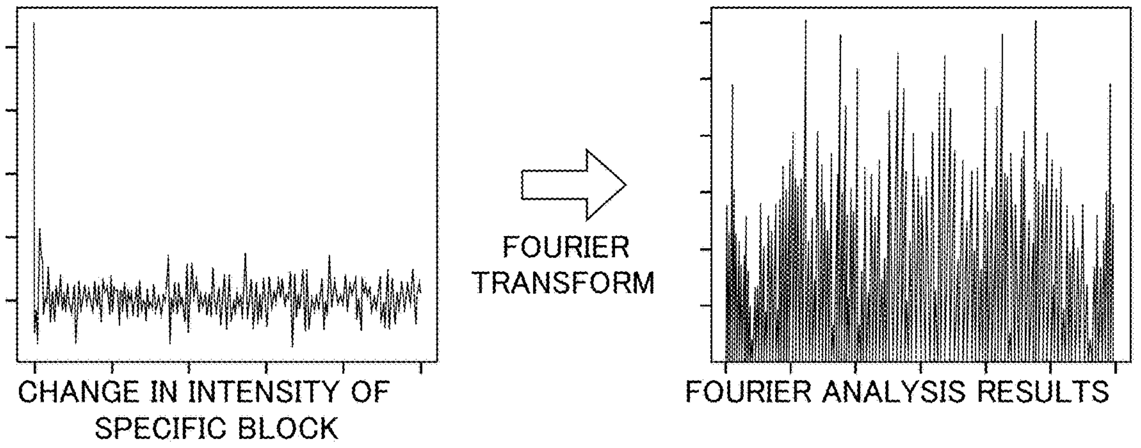
FIG. 3A is a diagram showing a change in “intensity” in a specific block and a result obtained by performing Fourier analysis thereof.
Figure 3B:
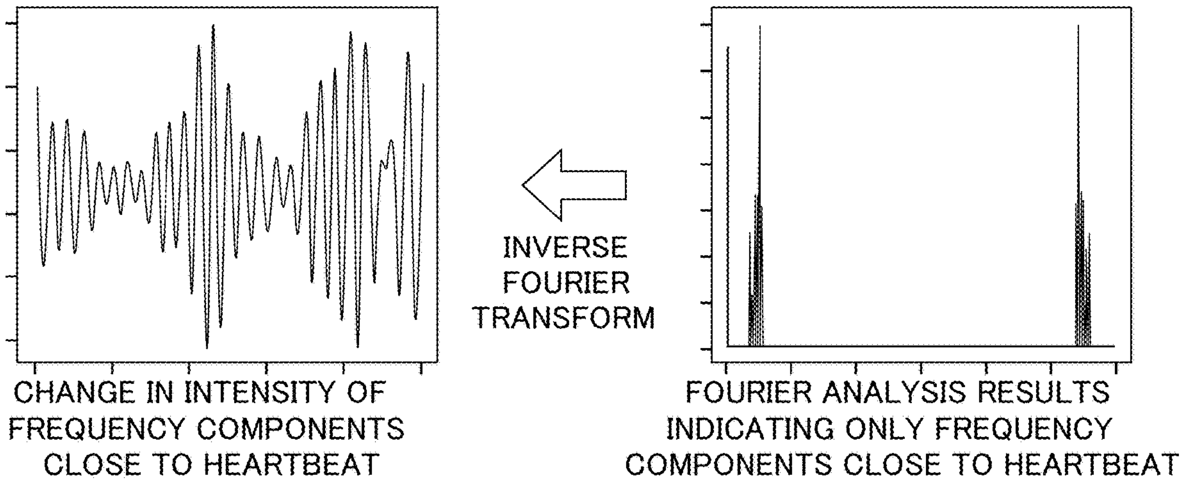
FIG. 3B is a diagram showing a Fourier transform result obtained by extracting frequency components close to a heartbeat and a change in “intensity” of frequency components close to a heartbeat, that is obtained by performing inverse Fourier transform on this.

Based on the cardiac movement cycle and the blood vessel beat cycle that are analyzed as described above, Fourier analysis is performed for the value of density/ intensity in each block area and a change amount thereof. FIG. 3A is a diagram showing a change in intensity in a specific block and a result obtained by performing Fourier analysis thereof. FIG. 3B is a diagram showing a Fourier transform result obtained by extracting frequency components close to a heartbeat and a change in intensity of frequency components close to a heartbeat, that is obtained by performing inverse Fourier transform on this. For example, when the change in intensity in a specific block is Fourier-transformed (Fourier analysis), the results as shown in FIG. 3A are obtained. Then, the results as shown on the right side in FIG. 3B are obtained by extracting the frequency components close to the heartbeat from the frequency components shown in FIG. 3A. By performing inverse Fourier transform on this, the change in intensity, that is tuned to the heartbeat can be obtained as shown on the left side in FIG. 3B.

Herein, when performing inverse Fourier transform on the spectrum including frequency components, the inverse Fourier transform may be performed by taking into consideration both a frequency element (a heartbeat, and a cardiovascular beat frequency) specified from density in a heartbeat and a blood flow, and a spectrum band (BPF may be used); or based on the element of either one.

In addition, it is possible to use an AR method (Autoregressive Moving average model) so that calculation is carried out in a short time when performing Fourier transform. According to the AR method, there is a method of using a Yule-walker equation or a Kalman filter in an autoregressive moving average model, and it is possible to make up for the calculation by using Yule-walker estimates derived therein, a PARCOR method, or a least squares method. By doing this, it becomes possible to acquire an image close to real time, to assist the calculation, and to correct the artifact at a higher speed. It becomes possible to extract and display the nature of an image in each block area via such Fourier analysis.

Figure 3C:
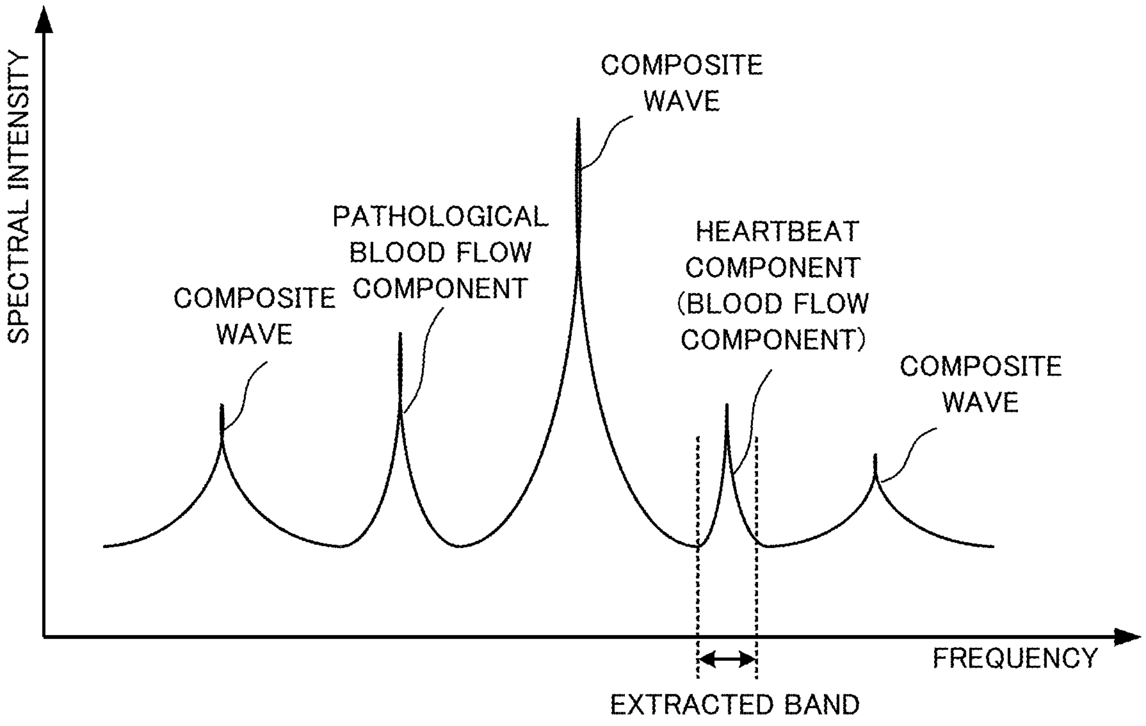
FIG. 3C is a diagram showing an example of extracting a certain fixed band out of a spectrum obtained after Fourier-transforming.

Herein, a spectrum in a fixed band including a spectrum corresponding to a cycle of the cardiac movement, out of a spectrum obtained after Fourier-transforming can be extracted by Fourier-transforming a change in an image in each block area in each frame image. FIG. 3C is a diagram showing an example of extracting a certain fixed band out of a spectrum obtained after Fourier-transforming. As to a frequency f of a composite wave spectrum, the relationship of "$1/f=1/f_1+1/f_2$" is satisfied between $f_1$ (a heartbeat component) and $f_2$ (a pathological blood flow component) of each frequency to be a composite source, and when extracting a spectrum, it is possible to employ the following method.

(1) A heartbeat having a high spectral ratio is extracted.
(2) A spectrum is extracted via division at a middle of the peak of a spectrum corresponding to a heartbeat/a pathological blood flow and the peak of a plurality of neighboring composite waves.
(3) A spectrum is extracted via division at the valley part of the peak of a spectrum corresponding to a heartbeat/a pathological blood flow and a spectrum of a plurality of neighboring composite waves.
(4) A spectrum included in a certain fixed bandwidth can be extracted from a heartbeat component (a blood flow component). In this case, a spectrum with a plurality of overlapping spectra is obtained, but by separating each component, each spectrum can be recovered.

As described above, according to the present invention, it does not mean that a fixed BPF is used, and a spectrum in a fixed band including a spectrum corresponding to a cycle of a cardiac movement is extracted. Further, according to the invention of the present application, it is possible to extract a frequency (for example, further, density/intensity in each region, and a heartbeat element obtained from a heartbeat or a blood vessel beat) other than a frequency of a cardiac movement obtained from a frame image, out of a spectrum obtained after the Fourier-transforming, or a spectrum in a fixed band including a spectrum (for example, spectral model) corresponding to a frequency input from the outside by an operator.

Herein, a composite wave spectrum element becomes 50%+50% in the case of having only two components (a heartbeat and a pathological blood flow), and in the case of three components, the distribution becomes one-third each. Thus, the composite wave spectrum can be calculated to some extent from what percentage the heartbeat component spectrum is and what percentage the pathological blood flow component spectrum is, and spectral components and height thereof. It is possible to extract the spectrum at a high ratio (%) thereof. That is, a ratio of a pathological blood flow component/heartbeat component to a composite wave component is calculated, and a spectral value having a high pathological blood flow component/heartbeat component is calculated and extracted. In addition, as to identification of diaphragm, there are some cases where only a spectrum or superimposed one thereof corresponding to a region in which Hz (frequency) becomes relatively constant, that is, an area in which a change in Hz is small is extracted from data obtained by acquiring frequencies of the heartbeat and the heart blood vessels. Further, in the case of determining a spectral band, there are some cases of determining the spectral band in a range where a change in Hz is generated, and an area on the periphery thereof. As a result of this, it becomes possible to extract, not only the case of being exactly consistent with the cycle of the cardiac movement or the blood vessel beat cycle, but also the spectrum that should be taken into consideration, and to make a contribution to an image diagnosis.

In addition, it is known that a "heartbeat" and "respiration" are included in a specific frequency band. Accordingly, by using, for example, a filter of "0~0.5 Hz (respiratory rate 0~30 times/min)" in the case of the respiration, and for example, a filter of "0.6~2.5 (heartbeat/pulse rate 36~150 times/min) Hz" in the case of a circulatory system, it is possible to specify a respiratory frequency and a frequency of a circulatory system using the foregoing filter, in advance. This enables displaying a frequency tunable image. This is because there is a case where a change in density of respiration (lung) is picked up when acquiring a change in density of a heart, and a change in density of a heart is picked up when acquiring a change in density of a lung.

[Waveform Analysis]

Waveform analysis is performed on a heart, blood vessels, electroencephalogram, and others that are recognized as constant waveforms in examinations. This includes movements that are repeated in a constant state such as foot movements. Also, analysis of whether there is the same tendency or not is performed by superimposing the Hz of repeated movements. The waveform data is compared and the concordance rate between two pieces of data is calculated. Then, the data after Fourier analysis is compared.

[Digital Filter]

Further, instead of the Fourier analysis described above, a digital filter can be used. The digital filter performs a transformation between the time domain and the frequency domain based on the "fast Fourier transform and inverse fast Fourier transform" that are mathematical algorithms for extracting frequency components of a signal in order to adjust them. This enables obtaining the same effect as the Fourier analysis described above.

[Visualization/Digitization]

The results of the above-described analysis are visualized and digitized. As the standard uptake, the value is often displayed relatively/logarithmically by having the average value as 1 from density/intensity in the entire area of the measured lung field. Further, since only the blood flow direction is employed, the change to a specific direction is often cut out. By doing this, it becomes possible to take out only data of a significant method. The pseudo colorization is performed following a change in an analysis range by using the identification result of the cardiac region. That is, the analysis result of each individual (subject) is fitted to a relative area in accordance with a specific shape (minimum, maximum, mean, median) fitted to the phase. Further, deformation is made to a specific shape/phase capable of comparing a plurality of analysis results therewith.

Further, when preparing a "standard heart," the above-described results of the analysis of the movement of the heart are used to calculate the relative positional relationship within the heart (myocardium). A "standard heart" is prepared by using a line that comprehensively averages contour lines, density, and the like of hearts of a plurality of patients. In addition, this concept is not limited to a heart, but can be applied to lungs (standard lungs) and other organs (standard organs). For example, it is possible to create "organ models" by age, gender, country, and degree of disease.

In addition to the above changes in the pixel values of the heart, it is also possible to perform Fourier analysis by calculating changes in the distance from the center of the heart to the myocardium (distance L shown in FIGS. 2B and 2C), and furthermore, it is possible to perform Fourier analysis by calculating changes in the volume of the heart.

After the "standard heart" is prepared, as described above, it becomes possible that tunability, a concordance rate, and a non-concordance rate are digitized and presented (display of a frequency tunable image). In addition, deviation from a normal state can be displayed. According to the present embodiment, discovery of a possibility of a new disease, comparison with oneself in the normal state, comparison of a hand with a foot, and comparison of another hand and another foot on the opposite side are made to be possible by performing Fourier analysis. Further, it becomes possible to grasp which portion is abnormal in a movement of the foot, deglutition or the like by digitizing the tunability. Further, it becomes possible to determine whether or not a person in the disease state changed after a fixed time elapses, and in addition, in the case where the person changed, it becomes possible to compare the states before and after the change.

[Drawing of a Heart]

In the present specification, a method of adjusting a heart so as to obtain a high matching property by tentatively drawing a contour of a heart by using a combination of Bezier curves and straight lines is employed. For example, when a contour of a heart is expressed with 4 Bezier curves and one straight line, it becomes possible to draw a contour of a heart by finding 5 points on the contour of the heart and 4 control points. It becomes possible to detect the contour of the heart with high accuracy by displacing the position of a point to draw a plurality of contours of the heart, and evaluating a matching property by using a condition under which "the total value of density inside the contour becomes the maximum", "the difference of a sum in density for a few pixels inside and outside the contour line becomes the maximum", or the like. In addition, it is also possible to extract the point near an outer edge by contour extraction via classical binarization, and to adjust the control point position of a Bezier curve by using a least squares method or the like. Further, the above method is not limited to s heart, but can be applied to other organs as "detection of organ." This is applicable not only to planar images but also to stereoscopic images (3D images). It becomes possible to presume a target surrounded by a plurality of curved surfaces to be an organ by defining a curved surface equation to set the control point thereof.

[Cardiac Function Analysis Using Fourier Analysis]

Figure 4:
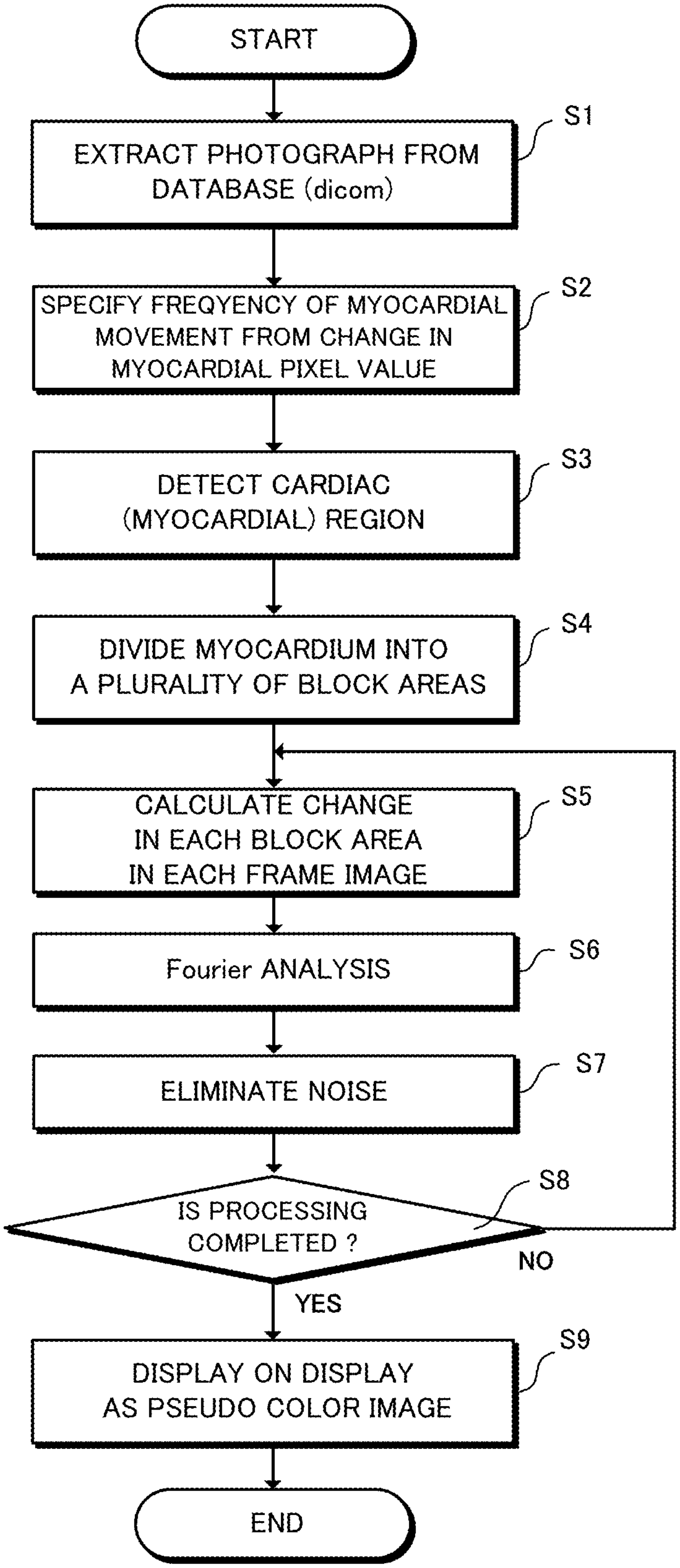
FIG. 4 is a flowchart showing an outline of image processing according to the present embodiment.

Next, the cardiac function analysis using Fourier analysis according to the present embodiment is explained. FIG. 4 is a flowchart showing an outline of the cardiac function analysis according to the present embodiment. The basic module 1 extracts images of DICOM from the database 15 (step S1). Herein, at least a plurality of frame images included within one heartbeat is acquired. Next, in each acquired frame image, the cycle of the movement of the heart is specified by using changes in pixel values, for example, changes in density (density/intensity), at least in a certain fixed area of the myocardium (step S2). Then, the cardiac (myocardial) region is detected (step S3), and the detected myocardium is divided into a plurality of block areas (step S4). Here, as described above, the myocardium is divided radially from the center of the heart by using Voronoi tessellation (Thiessen tessellation). Then, a change in pixel values in each block area in each frame image is calculated (step S5). Herein, values of changes within each block area are averaged and expressed as one piece of data.

In addition, it is also possible to vaguely display the pixel to a certain extent, display the whole by making it into a dimmed state. Specifically, in the case of blood vessels, a low signal value coexists between high signal values, but if only the high signal values can be roughly grasped, it is acceptable to be vague as a whole. For example, in the case of a blood flow, only a signal having a threshold or more may be extracted. Specifically, in the case where a numerical value in the following table is taken as one pixel, and the numerical value in the center is acquired, when a ratio occupied by the numerical value in the center is acquired and averaged within one pixel, the expression thereof can be smoothly made between neighboring pixels.

TABLE 1

| | | |
|---|---|---|
| 1 | 1 | 1 |
| 1 | 2 | 1 |
| 1 | 1 | 1 |

In addition, as to the change values within each block area, the noise elimination may be carried out by cut-off. Next, Fourier analysis is performed based on the cycle of the above-described cardiac movement, for the value of density/intensity in each block area and a change amount thereof (step S6). By doing this, it becomes possible to extract and display the nature of an image in each block area.

Herein, a spectrum in a fixed band including a spectrum corresponding to a cycle of the heart, out of a spectrum obtained after Fourier-transforming, can be extracted. Herein, as to a frequency f of a composite wave spectrum, the relationship of "$1/f=1/f_1+1/f_2$" is satisfied between $f_1$ and $f_2$ of each frequency that becomes a composite source, and when extracting a spectrum, it is possible to employ the following method.

(1) A movement of a heart having a high spectral ratio is extracted.

(2) A spectrum is extracted via division at a middle of the peak of a spectrum corresponding to a heartbeat/a blood flow and the peak of a plurality of neighboring composite waves.

(3) A spectrum is extracted via division at the valley part of the peak of a spectrum corresponding to a heartbeat/a blood flow and a spectrum of a plurality of neighboring composite waves.

Herein, a composite wave spectrum element becomes 50%+50% in the case of having only two components (a heartbeat and a pathological blood flow), and in the case of three components, the distribution becomes one-third each. Thus, the composite wave spectrum can be calculated to some extent from what percentage the heartbeat component spectrum is and what percentage the blood flow component spectrum is, and spectral components and height thereof. It is possible to extract the spectrum at a high ratio (%) thereof. That is, a ratio of a blood flow component/heartbeat component to a composite wave component is calculated, and a spectral value having a high blood flow component/heartbeat component is calculated and extracted.

Next, noise elimination is carried out for the results obtained by the Fourier analysis (step S7). Herein, the cut-off as described above and elimination of the artifact can be carried out. The above-described operation from step S5 to step S7 is performed at least once, and whether or not to be completed is determined (step S8). When not being completed, a transition is made to step S5; and when being completed, the results obtained by the Fourier analysis are displayed on the display as a pseudo color image (step S9). In addition, a black and white image may be displayed. There are some cases where the accuracy of data is improved by repeating a plurality of cycles in this manner. Thus, a desired moving image is possible to be displayed. Further, the desired moving image may be obtained by correcting the image displayed on the display.

In addition to the processing of division of the myocardium in steps S4 and S5 as described above, it is also possible to perform Fourier analysis by calculating the change in the distance from the center of the heart to the myocardium instead of steps S4 and S5.

[Cardiac Function Analysis Using a Digital Filter]

Figure 5:
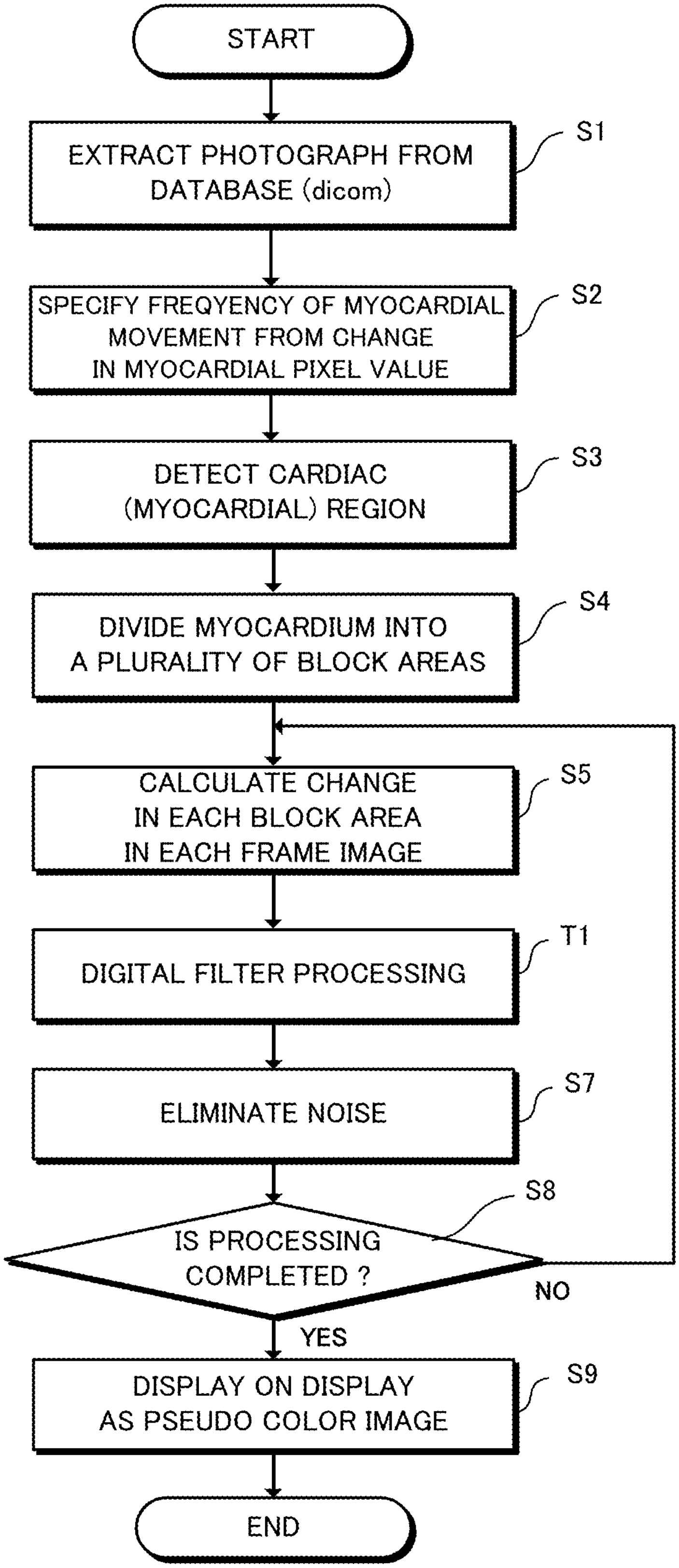
FIG. 5 is a flowchart showing an outline of image processing according to the present embodiment.

Next, cardiac function analysis using a digital filter according to the present embodiment is explained. FIG. 5 is a flowchart showing an outline of the cardiac function analysis according to the present embodiment. Steps S1 to S5 and S7 to S9 are the same as the "Cardiac function analysis using Fourier analysis" described above, and are therefore omitted. In the step T1 in FIG. 5, digital filter processing is performed (step T1). The digital filter performs a transformation between the time domain and the frequency domain based on the "fast Fourier transform and inverse fast Fourier transform" that are mathematical algorithms for extracting the frequency components of a signal in order to adjust them. This enables obtaining the same effect as the Fourier analysis described above.

[Cardiac Function Analysis Using a Tunable Concordance Rate]

Figure 6:
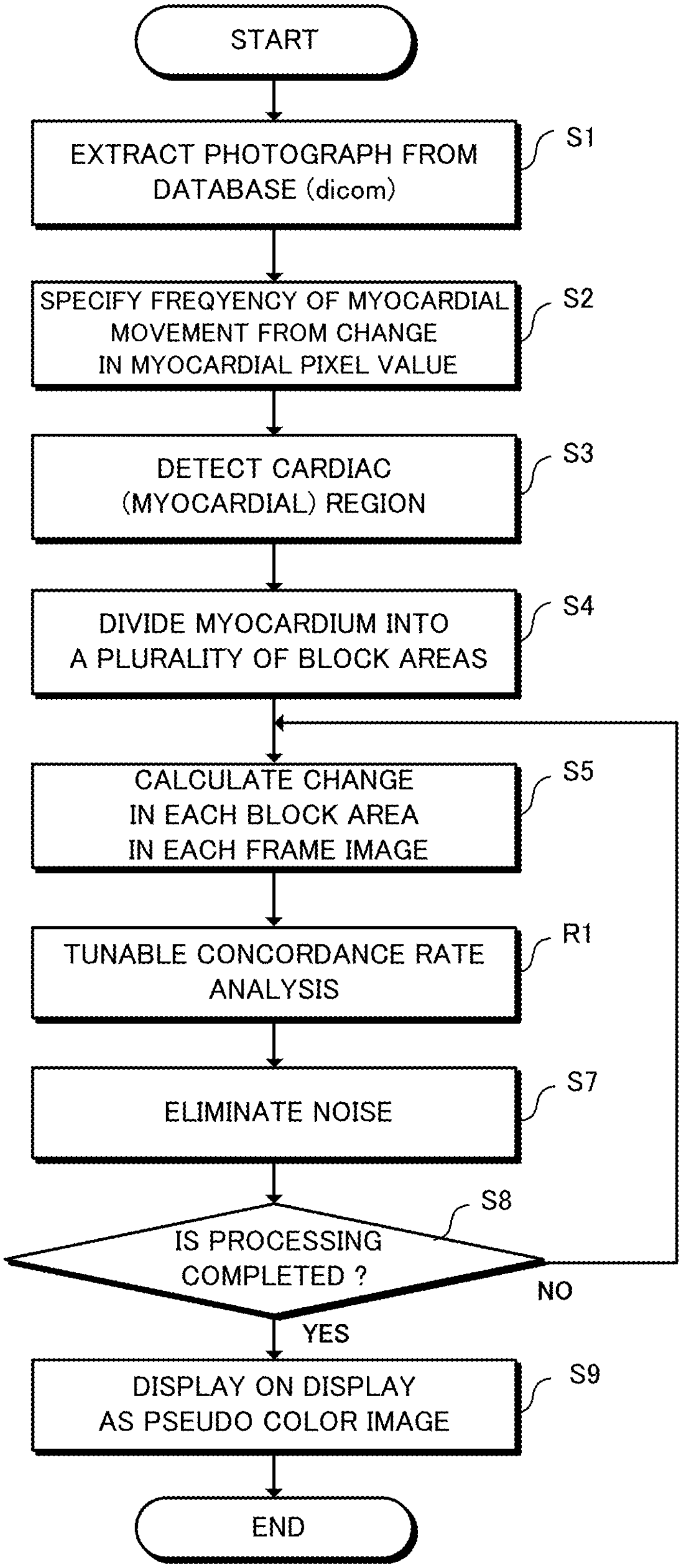
FIG. 6 is a flowchart showing an outline of image processing according to the present embodiment.

Next, cardiac function analysis using a tunable concordance rate according to the present embodiment is explained. FIG. 6 is a flowchart showing an outline of the cardiac function analysis according to the present embodiment. Steps S1 to S5 and S7 to S9 are the same as the "Cardiac function analysis using Fourier analysis" described above, and are therefore omitted. In step R1 in FIG. 6, analysis of a tunable concordance rate is performed (step R1). Therefore, the cardiac (myocardial) region is detected (step S3), and after the myocardium is divided into a plurality of block areas (step S4), average density (pixel value x) of block areas in each frame image is calculated, and a ratio (x') of an average pixel value of the block areas in each frame image to a change width (0% to 100%) from the minimum value to the maximum value of average density (pixel value x) is calculated (step S5). On the other hand, a ratio value (x'/y') of a ratio (y') of a change (y) in a heart of each frame image to a change width (0% to 100%) from the minimum to the maximum of a surface area (or volume) of a heart is calculated (step S5). By using them, only block areas for which the ratio value (x'/y') is within a predetermined fixed range can be extracted (step R1).

Herein, the case where y'=x' or y=ax (a represents a numerical value of a surface area or volume of a heart, or a coefficient of a numerical value of density) means complete concordance. However, it does not mean that only the case of the complete concordance indicates a meaningful value, and a value having a certain fixed width should be extracted. Thus, according to one aspect of the present embodiment, a fixed width is determined using logarithms (log), as described below. That is, when calculated at a ratio (%) in the case where y=x, complete concordance of tunability is "log Y'/x'=0". Further, when extracting one in which a range of a tunable concordance rate is narrow or a (numerically narrow) range, for example, it is determined as "log Y'/x'=−0.05~+0.05" in the range that is close to 0, and when being one in which a range of a tunable concordance rate is wide or a (numerically wide) range, for example, it is determined as "log Y'/x'=−0.5~+0.5" in the range that is close to 0. As this range is narrower, and the numerical value that is concordant within the range is also higher, the tunable rate can be said to be higher. When counting the number by determining this ratio value for each pixel of the pixels, a normal distribution in which the case of complete concordance is taken as a peak is obtained in the case of healthy persons. In contrast, in the case of those having disease, a distribution of this ratio value is to be lost. In addition, as described above, the method of determining a width using logarithms is only one example, and the present invention is not limited thereto. That is, the present invention is one performing "image extraction" as the following: (average of a change in density in a rough range)≈(a heartbeat)≈(a change in a heart)≈(an electrocardiogram)≈(a change in a surface area and volume of a heart), and is also applicable to methods other than the method of using logarithms.

In addition, when considering 3D, by measuring a heartbeat, a surface area or volume of a heart, cardiac output, and a central blood flow amount with another device, it becomes possible to measure the "partial surface area of the heart," "partial volume of the heart," and "blood flow rate" in each area from these rates. As these quantitative measurements, if a surface area of a heart, volume of a heart, cardiac output, and a blood flow amount on the center side can be measured by another modality and the like, it becomes possible to estimate the estimated functional capacity from the amount of one frame, the rate thereof, and the change amount rate in the area. That is, in the case of cardiac function analysis, it becomes possible to estimate volume of a heart from a movement of a heart; in the case of blood flow analysis, it becomes possible to estimate a lung blood flow amount from cardiac output, and to estimate an estimated blood flow amount (rate) in bifurcated blood vessels drawn from the blood flow amount (rate) on the center side.

Further, as described above, determination is possible to be made with higher accuracy if the entire acquired database can be calculated, but time is often required in executing computer analysis. Thus, it is enabled to carry out calculation by extracting only a certain fixed number (phase) thereof. For example, the acquisition is automatically made not from the beginning of the acquired images, but from the latter half of the images, namely, from the middle to the back of the images, not to the end (manual acquisition is also possible). This makes it easier to extract more stable images by cutting out the images photographed in tense state when the patient is photographed for the first time. In addition, instead of calculating the acquired images (foe example, 300 images) as they are, the change in a "movement of a heart" based on the first measured position of the heart, or the like, can be selected, and then calculated. This enables image labeling that looks like a continuous heartbeat when moving image labeling or the like needs to be repeated. In this case, calculation can be made by image labeling. In addition, when identifying the cardiac (myocardial) region, even in cases when manually changing the shape of only a part thereof or manually changing only a part of the graph labeling, it is desirable to correct the graph by using noise cutting and a least squares method.

As explained above, according to the present embodiment, it becomes possible to evaluate images of a human body with an X-ray moving image device. If digital data can be obtained, it is possible to calculate with existing facility devices in a generally excellent manner, and thus installation cost is reduced. For example, according to the X-ray moving image device provided with a Flat panel detector, it becomes possible to simply complete the examination of a subject. In cardiac function analysis, screening of myocardial infarction becomes possible. For example, according to the X-ray moving image device provided with the Flat panel detector, useless examinations can be eliminated by executing a diagnostic support program according to the present embodiment before performing CT. Further, the simple examination is carried out, and thus it becomes possible to find a disease with high urgency at an early stage and to preferentially treat it. According to the photographing method at present, in the case of another modality such as CT, MR or the like, there are some problems, but a detailed diagnosis in each area becomes possible if the foregoing problems can be solved.

Further, it is also applicable to screening of various kinds of blood vessels, for example, cervical blood flow narrowing; and is also applicable to the blood flow evaluation and screening of large blood vessels. Further, it is also possible to be applied for grasping characteristic conditions before and after surgery. Further, by Fourier-transforming a cycle of a movement of a heart and a blood flow cycle to eliminate a waveform of a movement of a heart and a blood flow waveform, in an X-ray image of an abdomen, it becomes possible to observe abnormality in a remaining biological movement, for example, intestinal tract ileus or the like.

In addition, when an image acquired at first exhibits high resolution to a certain extent, the number of pixels is large, and thus it often takes time for calculation. In this case, the calculation may be made after reducing the image to a fixed number of pixels. For example, it is possible to reduce the calculation time via the calculation made after reducing pixels of [4000×4000] to pixels of [1028×1028].

In addition, conventionally, the contrast range of the target image to be determined has been manually adjusted; or, a method of relatively extracting the target image to be determined based on a certain standard has been employed. However, it has not been performed strictly with the recognition of the frame of the analysis target (for example, a lung field). By detecting the cardiac region and filtering the bone density (cutting a certain range of low permeability) according to the present invention, the width of the permeability inside the rest of the region is to be strictly limited to the width of the recognized region of the heart. This enables stricter adjustment for determinable permeability, in a detection of a cardiac region, when it is viewed by a person who makes a determination, for example, a doctor, a technologist, or the like. Also, it enables stricter adjustment for permeability that is just right for evaluation of coloring.

In addition, in XP and CY, X-ray transmission is changed according to the body condition in order to reduce exposure. During photographing, the transmission may be changed depending on the movement of lungs. In addition, also in MRI, due to changes in the magnetic field in certain directions, or the like, the image is to be photographed with a certain non-uniform signal. In contrast, the change in "density/intensity" of a specific organ can be measured more precisely by adjusting the calculation of returning the transmittance changed from the transmittance of the surrounding "back ground" to a constant form, to the transmittance of the specific organ, or by applying a certain fixed correction to the signal value through correcting the non-uniformity of the overall change in a magnetic field to uniformity. In addition, more accurate change amount can be calculated by changing the degree of transmittance based on the characteristics of each organ from the numerical changes in photographing conditions and precisely correcting the change in "density/intensity" of a specific organ.

In the present invention, the average value or a change in intensity may be calculated, but the data (intensity) obtained from X-rays, CT, or the like, may be subject to "Gamma correction," and the density may not be reflected correctly. This Gamma correction is processing to correct the saturation and brightness of images or the like displayed on a display. Normally, a computer displays images on a display depending on the input signal, but the brightness and saturation may vary depending on the characteristics of the display. Therefore, Gamma correction is used to correct these errors. Gamma correction adjusts the relative relationship of signals and color data as they are input to and output from the display, resulting in a more natural-looking display. However, since an image after gamma correction is no longer the original image, it may cause inconvenience when applying the image processing according to the present invention. Therefore, the image before Gamma correction is obtained by applying "Gamma inverse correction," namely, the inverse filter corresponding to the Gamma correction value, to the image after Gamma correction. This enables obtaining the image before Gamma correction, which enables the image processing according to the present invention to be performed properly.

In addition, the present invention is not limited to Gamma correction, and an image having undergone other image processing may be restored and then subjected to processing. For example, from the changes in pixel values in a region where density is invariant during photographing, such as a space outside the human body, the image processing performed on the image is analogized, and a function that keeps the changes in pixel values constant is applied to all pixels. This enables obtaining an image that is close to the original image and enables the image processing according to the present invention to be performed properly.

In addition, the present invention is capable of restoring individual images from superimposed images. Conventionally, "X-ray difference image technology" is known. This technology superimposes "past and present X-ray images" of the same patient photographed during medical checkups, or the like, and emphasizes areas changed from the past to the present, namely, areas that are assumed to be abnormal. By doing this, for example, it becomes possible to detect cancer at an early stage. As a method of superimposition, when a plurality of images is photographed as "the first, second, third, fourth ones . . . ", for example, "the first, second, and third ones" are used as "the superimposed image of the first one"; "the second, third, and fourth ones" are used as "the superimposed image of the second one"; and "the third, fourth, and fifth ones" are used as "the superimposed image of the third one." As for such superimposed images, the pixel values are higher where a plurality of images overlap, and lower where they do not overlap. Since such superimposed images may blur the contours of the organs, it is desirable to restore them to their respective original images. According to the present invention, the contours of the organs can be identified, which enables restoring the original image from the superimposed image.

In addition, the present invention also enables imaging the difference in a frequency of each region in an organ. In other words, in organs with cyclic movements, the change values for each region can be Fourier-transformed, and weighted such as classifying each region by colors based on the composition ratio of frequency components, to show the characteristics of each region. For example, it is possible to identify the frequency components that peak in each region and classify each region by colors. Further, in each region, it is also possible to identify the percentage of each frequency component within a specific frequency band, and classify each region by colors depending on the percentage. Further, in a specific region, the frequency composition ratio to be the standard is, for example, "50% for 10 Hz and 50% for 20 Hz," it is also possible to visualize the rate of deviation from the frequency composition ratio to be the standard. In this way, for example, for a heart, by displaying the spectrum distribution of a frequency with classifying by colors, it becomes possible to grasp at a glance whether a correct movement is made or an incorrect movement is made.

EXPLANATION OF THE SYMBOLS

1 basic module
3 cardiac function analysis unit
5 blood flow analysis unit
7 another blood flow analysis unit
9 Fourier analysis unit
10 waveform analysis unit
11 visualization/digitization unit
13 input interface
15 database
17 output interface
19 display

The invention claimed is:

1. A diagnostic support system, comprising a computer configured to execute a diagnostic support program that analyzes images of an organ of a human and displays analysis results, the computer being configured to perform;
- acquiring a plurality of frame images;
- calculating a cyclic change that characterizes a state of the organ between each of the frame images;
- Fourier-transforming the cyclic change;
- extracting a spectrum in a fixed band including a spectrum corresponding to a frequency of movement of the organ, out of a spectrum obtained after the Fourier-transforming;
- performing inverse Fourier transform on the spectrum extracted from the fixed band; and
- outputting each of the images after performing the inverse Fourier transform and displaying the images on a display, wherein the computer is further configured to extract, for each pixel in a specific frame image, pixels having different coordinates in subsequent frame images, to calculate a cyclic change that characterizes the state of the organ, and to output images after performing Fourier transform, spectral extraction, and inverse Fourier transform.

2. A diagnostic support system, comprising a computer configured to execute a diagnostic support program that analyzes images of an organ of a human and displays analysis results, the computer being configured to perform:
- acquiring a plurality of frame images;
- calculating a cyclic change that characterizes a state of the organ between each of the frame images;
- Fourier-transforming the cyclic change;
- extracting a spectrum in a fixed band including a spectrum corresponding to a frequency of movement of the organ, out of a spectrum obtained after the Fourier-transforming;
- performing inverse Fourier transform on the spectrum extracted from the fixed band;
- outputting each of the images after performing the inverse Fourier transform and displaying the images on a display, and
- wherein the computer is further configured to extract pixels that change corresponding to a frequency of the cyclic change by a digital filter, and to output images including the pixels extracted by the digital filter.

3. The diagnostic support system according to claim 2, wherein the computer is further configured to divide images of the organ into a plurality of block areas, to calculate a change in an image in each block area, and to perform said Fourier transform and inverse Fourier transform based on the calculated change.

4. The diagnostic support system according to claim 2, wherein the computer is further configured to divide an analysis range into a plurality of areas by using a Voronoi tessellation method.

5. The diagnostic support system according to claim 2, wherein the computer is further configured to classify each of the areas based on an index of a cyclic change for each of the divided areas.

6. The diagnostic support system according to claim 2, wherein the computer is further configured to calculate a cyclic change that characterizes the state of the organ while maintaining an absolute positional relationship of each pixel in the plurality of frame images.

7. The diagnostic support system according to claim 6, wherein the computer is further configured to extract pixels that change corresponding to a frequency of the cyclic change by a digital filter, and to output images including the pixels extracted by the digital filter.

8. The diagnostic support system according to claim 6, wherein the computer is further configured to select a color corresponding to the cyclic change rate that characterizes the state of the organ, and to add the selected color on the change rate of the pixel values for display.

9. The diagnostic support system according to claim 2, wherein the computer is further configured to classify a plurality of frame images into a plurality of groups and to calculate a cyclic change while maintaining the absolute positional relationship of each pixel in the frame images belonging to each group.

10. The diagnostic support system according to claim 2, wherein the computer is further configured to correct a signal value of an area where a magnetic field of MRI is nonuniform in a frame image, and to convert it into an image obtained when a magnetic field is uniform.

11. The diagnostic support system according to claim 2, wherein the computer is further configured to calculate a change rate from a change in the entire organ between each of the frame images, and to calculate a change in block areas based on the calculated change rate.

12. The diagnostic support system according to claim 2, wherein the change rate changes depending on a position of the block areas in the organ or is constant throughout the organ.

13. The diagnostic support system according to claim 2, wherein the computer is further configured to set a maximum outer edge when the size of the organ is maximum, to set a minimum outer edge when the size of the organ is minimum, and to calculate coefficients of outer edges of organs of other sizes by using the maximum and minimum outer edges, and to display a waveform corresponding to the coefficients on a graph.

14. The diagnostic support system according to claim 13, wherein the computer is further configured to change the coefficients of the waveform by varying positions of control points on the graph.

15. The diagnostic support system according to claim 2, wherein the computer is further configured to display a pixel average value of the image of the organ on the graph.

16. The diagnostic support system according to claim 2, wherein the computer is further configured to display the image of the organ juxtaposed with the graph.

17. The diagnostic support system according to claim 2, wherein the computer is further configured to classify each block area by colors based on a composition ratio of frequency components after Fourier analysis.

18. The diagnostic support system according to claim 2, wherein the computer is further configured to extract, for each pixel in a specific frame image, pixels having different coordinates in subsequent frame images, to calculate a cyclic change that characterizes the state of the organ, and to output images after performing Fourier transform, spectral extraction, and inverse Fourier transform.

19. A diagnostic support system, comprising a computer configured to execute a diagnostic support program that analyzes images of an organ of a human and displays analysis results, the computer being configured to perform:

acquiring a plurality of frame images;

calculating a cyclic change that characterizes a state of the organ between each of the frame images;

Fourier-transforming the cyclic change;

extracting a spectrum in a fixed band including a spectrum corresponding to a frequency of movement of the organ, out of a spectrum obtained after the Fourier-transforming;

performing inverse Fourier transform on the spectrum extracted from the fixed band;

outputting each of the images after performing the inverse Fourier transform and displaying the images on a display, and, wherein the computer is further configured to select a color corresponding to the cyclic change rate that characterizes the state of the organ, and to add the selected color on the change rate of the pixel values of the organ images for display.

* * * * *